(12) United States Patent
Bruns et al.

(10) Patent No.: US 10,983,122 B2
(45) Date of Patent: Apr. 20, 2021

(54) DIAGNOSTIC METHODS FOR THE DETECTION AND QUANTIFICATION OF BLOOD-RELATED DISEASES

(71) Applicant: ADOLPHE MERKLE INSTITUTE, UNIVERSITY OF FRIBOURG, Fribourg (CH)

(72) Inventors: Nico Bruns, Merzhausen (DE); Omar Rifaie Graham, Marly (CH); Jonas Pollard, Fribourg (CH)

(73) Assignee: ADOLPHE MERKLE INSTITUTE, UNIVERSITY OF FRIBOURG, Fribourg (CH)

( * ) Notice: Subject to any disclaimer, the term of this patent is extended or adjusted under 35 U.S.C. 154(b) by 247 days.

(21) Appl. No.: 16/301,791

(22) PCT Filed: May 19, 2017

(86) PCT No.: PCT/EP2017/062169
§ 371 (c)(1),
(2) Date: Nov. 15, 2018

(87) PCT Pub. No.: WO2017/198850
PCT Pub. Date: Nov. 23, 2017

(65) Prior Publication Data
US 2019/0154685 A1 May 23, 2019

Related U.S. Application Data

(60) Provisional application No. 62/338,673, filed on May 19, 2016.

(51) Int. Cl.
*G01N 33/72* (2006.01)
*G01N 33/557* (2006.01)
(Continued)

(52) U.S. Cl.
CPC ..... *G01N 33/56905* (2013.01); *C08F 220/56* (2013.01); *G01N 21/33* (2013.01);
(Continued)

(58) Field of Classification Search
CPC .. C08F 220/56; G01N 21/33; G01N 2650/00; G01N 33/557; G01N 33/56905;
(Continued)

(56) References Cited

U.S. PATENT DOCUMENTS

2010/0324201 A1* 12/2010 Caneba ............... C08F 293/00
524/568

FOREIGN PATENT DOCUMENTS

WO 2016020534 A1 2/2016

OTHER PUBLICATIONS

Pollard et al. Analytical Chemistry, vol. 92, Dec. 2, 2019, pp. 1162-1170.*
(Continued)

*Primary Examiner* — Maureen Wallenhorst
(74) *Attorney, Agent, or Firm* — Hudak, Shunk & Farine Co. LPA

(57) ABSTRACT

A diagnostic method suitable for detection and quantification of blood-related diseases or conditions. The methods utilize biomarkers, such as hemoglobin and hemozoin as catalysts in an atom transfer radical polymerization (ATRP) reaction performed above a lower critical solution temperature (LCST) of a polymer which allows the polymerization to be tracked by rate of turbidity formation. The rate of turbidity formation is correlated to the concentration of the biomarker, making the tests useful quantitative techniques which can be utilized as point-of-care tests in the field.

15 Claims, 16 Drawing Sheets

(51) Int. Cl.
　　　G01N 33/573　　(2006.01)
　　　G01N 21/33　　(2006.01)
　　　G01N 33/569　　(2006.01)
　　　C08F 220/56　　(2006.01)
(52) U.S. Cl.
　　　CPC ......... *G01N 33/557* (2013.01); *G01N 33/573* (2013.01); *G01N 33/721* (2013.01); *G01N 2650/00* (2013.01); *Y02A 50/30* (2018.01)
(58) Field of Classification Search
　　　CPC .... G01N 33/573; G01N 33/721; G01N 33/48; G01N 33/49; G01N 33/493
　　　USPC ......... 436/63, 66, 164, 174, 177; 435/27, 28
　　　See application file for complete search history.

(56) References Cited

OTHER PUBLICATIONS

Raccio et al. Analyst, DOI:10.1039/d0an00976h, Sep. 17, 2020, pp. 1-11.*
Rifaie-Graham et al. Nature Communications, vol. 10, issue 1, Mar. 25, 2019, pp. 1-8.*
Nyunt et al., Detection of Plasmodium Falciparum in Pregnancy by Laser Desorption Mass Spectrometry, The American Journal of Tropical Medicine and Hygiene, 2005, vol. 73(3), pp. 485-490.
Butykai et al., Malaria Pigment Crystals as Magnetic Micro-Rotors: Key for High-Sensitivity Diagnosis, Scientific Reports, 2013, 3:1431, pp. 1-10.
Garrett et al., Bio-Sensing with Butterfly Wings: Naturally Occurring Nano-Structures for SERS-Based Malaria Parasite Detection, Physical Chemistry Chemical Physics, 2015, vol. 17, pp. 21164-21168.
E.Y.L. Hleb et al., Malaria Theranostics Using Hemozoin-Generated Vapor Nanobubbles, Theranostics, 2014, vol. 4, Issue 7, pp. 761-769.
Newman et al., A Magneto-Optic Route Toward the in Vivo Diagnosis of Malaria: Preliminary Results and Preclinical Trial Data, Biophysical Journal, 2008, vol. 95, pp. 994-1000.
Sigala et al., The Peculiarities and Paradoxes of Plasmodium Heme Metabolism, Ann. Rev. Microbiology, vol. 68, pp. 259-278, Jun. 16, 2014.
Traore et al., Flow-Injection Chemiluminescence Determination of Haemoglobin in the Blood, Luminescence, 2013, vol. 28, pp. 56-62.
Pourreza et al., Hemoglobin Detection Using Curcumin Nanoparticles as a Colorimetric Chemosensor, RSC Adv., 2015, vol. 5, pp. 1712-1717.
Silva et al., Hemoglobin and Red Blood Cells Catalyze Atom Transfer Radical Polymerization, BioMacromolecules, ACS Publications, 2013, pp. 2703-2712.
Hollmann et al., Enzyme Initiated Radical Polymerizations, Polymers ISSN 2073-4360, 2012, vol. 4, pp. 759-793.
Nakabayashi et al., Recent Progress in Controlled Radical Polymerization of N-vinyl Monomers, European Polymer Journal, 2013, vol. 49, No. 10, pp. 2808-2838.
Sigg et al., Horseradish Peroxidase as a Catalyst for Atom Transfer Radical Polymerization, Macromolecular Rapid Communications, 2011, vol. 32, No. 21, pp. 1710-1715.
Worldwide Prevalence of Anaemia 1993-2005, Geneva: World Health Organization, 2008.
The Global Prevalence of Anaemia in 2011, Geneva: World Health Organization, 2015.
Das et al., Quantitative Microscopy Approach for Shape-Based Erthrocytes Characterization in Anaemia, Journal of Microscopy, 2013, vol. 249, Pt. 2, pp. 136-149.
Nestel et al., Anemia Detection Methods in Low-Resource Settings: A manual for Health Workers, Program for Appropriate Technology in Health, 1997.

V. Han et al., A Comparative Study of Common Techniques Used to Measure Haemolysis in Stored Red Cell Concentrates, Vox Sanguinis, 2010, vol. 98, pp. 116-123.
Acker et al., An Analysis of the Bias in Red Blood Cell Hemolysis Measurement Using Several Analytical Approaches, Clinica Chimica Acta 413, 2012, pp. 1746-1752.
Tinker et al., Sodium Nitroprusside: Pharmacology, Toxicology and Therapeutics, Anesthesiology, 1976, vol. 45, No. 3, pp. 340-352.
Maiese et al., Peptide Growth Factors Protect Against Ischemia in Culture by Preventing Nitric Oxide Toxicity, The Journal of Neuroscience, 1993, vol. 13, pp. 3034-3040.
Shamsipur et al., Hemoglobin Detection Using Carbon Dots as a Fluorescence Probe, Biosensors and Bioelectronic, 2015, vol. 71, pp. 470-475.
Harboe, M., A Method for Determination of Hemoglobin in Plasma by Near-Ultraviolet Spectrophotometry, Scandinavian Journal of Clinical and Laboratory Investigation, 1959, vol. 11, pp. 66-70.
Oshiro et al., New Method for Hemoglobin Determination by Using Sodium Lauryl Sulfate (SLS), Clinical Biochemistry, 1982, vol. 15, pp. 83-88.
Schenck et al., Evaluation of "HemoCue", a New Device for Determining Hemoglobin, Clinical Chemistry, 1986, vol. 32, pp. 526-529.
Cao et al., A Fluorescent Sensor for the Detection of Multi-Molecule Species Based on Redox Reaction, Sensors and Actuators B: Chemical, 2015, vol. 208, pp. 50-53.
Morgner et al., Detecting Free Hemoglobin in Blood Plasma and Serum with Luminescent Terbium Complexes, Physical Chemistry Chemical Physics, 2015, vol. 17, pp. 1740-1745.
Pang et al., A Novel Fluorescence Assay for the Detection of Hemoglobin Based on the G-quadruplex/hemin Complex, Talanta 118, 2014, pp. 118-122.
Zo et al., Highly Differentiated Fluorescence Quenching of Hemoglobin Using a Stilbazolium Dye, Dyes and Pigments 101, 2014, pp. 38-42.
Matysiak et al., A Novel Type of Electrochemical Sensor Based on Ferromagnetic Carbon-Encapsulated Iron Nanoparticles for Direct Determination of Hemoglobin in Blood Samples, Biosensors and Bioelectronics, 2015, vol. 64, pp. 554-559.
Zhang et al., Molecularly Imprinted Photo-Sensitive Polyglutamic Acid Nanoparticles for Electrochemical Sensing of Hemoglobin, Microchim Acta, 2015, vol. 182, pp. 175-183.
Sun et al., Preparation of Hemoglobin (Hb) Imprinted Polymer by Hb Catalyzed eATRP and its Application in Biosensor, Biosensors and Bioelectronics, 2016, vol. 77, pp. 894-900.
S.E.H. Marosek, et al., Quantitative Determination of Hemoglobin in Tooth and Bone by UV/Vis Spectroscopy and cyclic Voltammetry, Journal of Forensic Research, 2013, vol. 4, Issue 2, pp. 1-5.
Li et al., G-Quadruplex DNAzymes-Induced Highly Selective and Sensitive Colorimetric Sensing of Free Heme in Rat Brain, Analyst, Royal Society of Chemistry, 2014, vol. 139, pp. 1993-1999.
Pourreza et al., Hemoglobin Detection Using Curcumin Nanoparticles as a Colorimetric Chemosensor, RSC Advances, 2015, vol. 4, pp. 1712-1717.
Lou et al., Radical Polymerization in Biosensing, Analytical and Bioanalytical Chemistry, 2006, 386, pp. 525-531.
Wu et al., Target-Triggered Polymerization for Biosensing, Accounts of Chemical Research, 2012, 45, pp. 1441-1450.
Malinowska et al., Enzyme- and Affinity Biomolecule-Mediated Polymerization Systems for Biological Signal Amplification and Cell Screening, Current Opinion in Biotechnology, 2016, 39, pp. 68-75.
Guo et al., Chemically Modified Chitosan Beads as Matrices for Adsorptive Separation of Proteins by Molecularly Imprinted Polymer, Carbohydrate Polymers, 2005, 62, pp. 214-221.
Gormley et al., Polymerization Amplified Detection for Nanoparticle-Based Biosensing, ACS Publications, Nano Letters, 2014, 14, pp. 6368-6373.
Simakova et al., Bioinspired Iron-Based Catalyst for Atom Transfer Radical Polymerization, Angewandte Chemie International edition, 2013, 125, pp. 12370-12373.

(56) References Cited

OTHER PUBLICATIONS

Yamashita et al., Atom Transfer Radical Polymerization of N-isopropylacrylamide by Enzyme Mimetic Catalyst, Polymer, 2013, 54, 1775-1778.

Harris et al., A Large Proportion of Asymptomatic Plasmodium Infections with Low and Sub-Microscopic Parasite Densities in the Low Transmission Selling of Temotu Province, Solomon Islands: Challenges for Malaria Diagnostics in an Elimination Setting, Malaria Journal, 2010, 9, p. 254.

T. Hanscheid, Diagnosis of Malaria: A Review of Alternatives to Conventional Microscopy, Clinical & Laboratory Haematology, 1999, 21, pp. 235-245.

Anthony Moody, Rapid Diagnostic Tests for Malaria Parasites, Clinical Microbiology Review, 2002, 15, pp. 66-78.

Wilson et al., Detection of Malarial Byproduct Hemozoin Utilizing its Unique Scattering Properties, Optics Express, 2011, vol. 19, No. 13, pp. 12190-12196.

Summary of Performance of Rapid Diagnostic Tests for Malaria: WHO Product Testing Rounds 1-6, 2008-2015, pp. 1-154.

Murray et al., Update of Rapid Diagnostic Testing for Malaria, Clinical Microbiology Reviews, Jan. 2008, vol. 21, No. 1, pp. 97-110.

Leo L.M. Poon et al., Sensitive and Inexpensive Molecular Test for Falciparum Malaria: Detecting Plasmodium Falciparum DNA Directly from Heat-Treated Blood by Loop-Mediated Isothermal Amplification, Clinical Chemistry, 2006, 52, pp. 303-306.

Desakorn et al., Semi-Quantitative Measurement of Plasmodium Falciparum Antigen PfHRP2 in Blood and Plasma, Transactions of the Royal Society of Tropical Medicine and Hygiene, 1997, 91, pp. 479-483.

Mens et al., Direct Blood PCR in Combination with Nucleic Acid Lateral Flow Immunoassay for Detection of Plasmodium Species in Settings Where Malaria is Endemic, Journal of Clinical Microbiology, Nov. 2012, vol. 50, No. 11, pp. 3520-3525.

Hofmann et al., Ultra-Sensitive Detection of Plasmodium Falciparum by Amplification of Multi-Copy Subtelomeric Targets, PLOS Medicine, 2015, pp. 1-21.

Mangold et al., Real-Time PCR for Detection and Identification of *Plasmodium* spp., Journal of Clinical Microbiology, 2005, vol. 43, No. 5, pp. 2435-2440.

Olivier et al., Malarial Pigment Hemozoin and the Innate Inflammatory Response, Frontiers in Immunology, 2014, vol. 5, Art. 25, pp. 1-10.

Coronado et al., Malarial Hemozoin: From Target to Tool, Biochimica et Biophysica Acta 1840, 2014, pp. 2032-2041.

Biot et al., Application of Inorganic Chemistry for Non-Cancer Therapeutics, Dalton Transactions, 2012, vol. 41, No. 21, pp. 6321-6580.

Scholl et al., Rapid Detection of Malaria Infection in vivo by Laser Desorption Mass Spectrometry, The American Journal of Tropical Medicine and Hygiene, 2004, vol. 71, pp. 546-551.

\* cited by examiner

DIAGNOSTIC METHODS FOR THE DETECTION AND QUANTIFICATION OF BLOOD-RELATED DISEASES

FIELD OF THE INVENTION

The present invention relates to diagnostic methods suitable for detection and quantification of biological sample-borne diseases or conditions. The methods utilize biomarkers, such as hemoglobin, hemozoin, hematin and heme as catalysts in an atom transfer radical polymerization (ATRP) reaction performed above a lower critical solution temperature (LCST) of a polymer which allows the polymerization to be tracked by rate of turbidity formation. The rate of turbidity formation is correlated to the concentration of the biomarker, making the tests useful quantitative techniques which can be utilized as point-of-care tests in the field.

BACKGROUND OF THE INVENTION

A myriad of diagnostic tests having been proposed in the art and literature to detect diseases and conditions afflicting mankind. Among the tests, various procedures have been proposed to detect hemoglobin and malaria, for example, as discussed below.

Hemoglobin

A decreased number of red blood cells (RBCs) or an insufficient concentration of hemoglobin in blood may cause a condition in which oxygen is not delivered in the required amounts to the cells. Such condition is named by the general term of "anemia". Anemia is normally caused by a deficiency of iron, but also by deficiencies of folate, vitamin A or vitamin B12, parasitic infections, chronic inflammations or genetic disorders. The World Health Organization (WHO) estimated 1.62 billion people affected by anemia in 2008 (24.8% of the world population)[1]. Anemia affects countries of low and high income, having an impact on economic and social development[2]. Though light microscopy can give information on the causes of certain types of anemia based on the shape and the count of the RBCs[3], it is a time consuming technique and requires of highly trained personnel. For this reason anemia is primarily identified based on physiological signs in non-invasive tests which measure hemoglobin levels. Non-invasive tests are generally based on the examination of the degree of pallor in eyelids, lips, tongue, gums and skin beneath the fingernails. The degree of pallor indicates the severity of anemia. The main disadvantage of this method is the subjectivity from the examiner and the variability between patients. This leads to the necessity for invasive methods of diagnosis. The hematocrit level measures the ratio of the volume of RBCs against the total volume of the blood after a centrifugation. Though this is a simple and fast method for anemia determination, it is highly dependent on the stability of the RBCs of a given sample. Therefore, direct hemoglobin determination methods become more interesting for anemia determination.

The Drabkin colorimetric assay is the most widely used method for hemoglobin quantification[5]. It is based on the oxidation and complexation of all hemoglobin species with cyanides to the stable cyanmethemoglobin (HiCN) form, excluding the traces of sulfhemoglobin[6,7]. The absorbance value at 540 nm is used to determine the concentration of cyanmethemoglobin. However, this method employs toxic reagents[8,9] and generates highly hazardous wastes[4,10-12]. In this regard, a series of alternative semiquantitative methods are available for the detection of hemoglobin. They are generally based on physical parameters. Some methods rely on the ability of blood to float in certain solutions. But most generally they are based on the color of treated or untreated dry blood against standard color strips or glass slides[4]. Though the previously mentioned methods have the advantage of being able to be used in low-cost settings, they have the main disadvantage of being subjective and being dependent on the sample preparation. Accurate quantitative spectroscopic methods have also been achieved[13-15], though the Drabkin colorimetric assay still remains the international gold standard for hemoglobin quantification. Unfortunately, these tests have difficulties determining low concentrations of hemoglobin[5,11] which may be useful for the detection of trace amounts in urine or mild hemolytic anemia. More sensitive methods including fluorimetryl[11,16-20], electrochemistry[21-25], colorimetry[26,27] or chemiluminscence[28] have been studied. The main drawback of these assays is that they involve complex instrumentation and expensive chemicals such as DNA aptamers or fluorescent dyes which can ultimately undergo photobleaching.

Polymers are recently driving attention for their ability to sense biomolecules[29-33]. Heme-containing proteins such as horseradish peroxidase or hemoglobin have the capacity to initiate free radical polymerizations[34]. Moreover, Bruns and coworkers showed that these enzymes can catalyze atom transfer polymerization (ATRP)[35,36]. These proteins do not only serve to initiate the polymerization reactions using an alkyl bromide initiator but also catalytically control the growth of the polymer chains. Water soluble polymers including N-isopropyl acrylamide (NIPAM) have been synthesized by biocatalytic ATRP. Hemin has also been shown to be a catalyst for ATRP[37,38].

Malaria

The WHO (World Health Organization) estimated 3.2 billion people at risk of being infected by the malaria disease and 1.2 billion at high risk in 2015. 214 million cases were reported ending in 438000 deaths. 90% of the deaths occurred in Africa, of which 95% were children aged under 5 years[39]. Malaria is caused by several *Plasmodium* species that undergo a complex life cycle. Diagnosis of malaria infections is one of the keys to eradicate the disease. For example, highly sensitive techniques for malaria diagnosis are needed to treat populations in endemic areas which are immune to the symptoms, but are still reservoirs of the parasite, allowing mosquitoes to be re-infected and spread the disease.[40] Microscopy is the most widely used technique to diagnose malaria (Giemsa staining)[41]. It allows the identification of the malaria species, and has a detection limit of 5 to 20 parasites/µl.[41] However, this method requires well-trained technicians, as it depends on the ability of the microscopist to correctly identify the parasite in a blood smear sample. As a result, there is a risk of misdiagnosis. This is the reason why malaria rapid diagnostic tests (MRDTs) have been developed by malaria control programs which can be applied in the field. Since the WHO recommended in 2010 the diagnosis of all suspected cases, the number of people using MRDTs has increased from less than 200 000 in 2005 to more than 314 million in 2014.[39] There are more than 200 MRDTs in the market which are in general based on immuno-chromatography strips that perform antigen-antibody complexation. The antigens detected are the Histidine Rich Protein 2 (HRP-2), Plasmodium Lactate Dehydrogenase (pLDH) and Plasmodium Aldolase[42]. By the combination of these, all the *Plasmodium* sp. can be detected. But none of these antigens are specific by themselves and some variants of species do not have these antigens. Also, there can be cross reactions with antigens of other parasites such as *Schistosoma mekongi*[43]. Another problem is that antibodies are labile and do not always perform as expected at the high and humid temperatures of the tropical regions[44]. Moreover, MRDTs show low sensitivities (above 100-200 parasites/pi)[45a,45b], and are unable to quantify parasitemia. Highly sensitive methods such as loop-mediated isothermal amplification (LAMP)[46] or enzyme linked immunosorbent assay (ELISA)[47] have been achieved, and efforts are being conducted to develop qPCRs for field work[48-50]. However, up to now these techniques can only be used in specialized laboratories.

Very few tests are based on the detection of hemozoin, hematin, or heme which are derivatives of the hemoglobin digestion of the malaria parasite[51-53]. Hemozoin is a biocrystal which is insoluble in physiological conditions, and consists of dimers of heme.[54] Hemozoin is a powerful biomarker for the malaria infection, since it is found in all clinically relevant *Plasmodium* species, i.e. it is a pan-malaria-species marker.[55] Moreover, all malaria parasites produce substantial amounts of it. Although microscopically visible hemozoin crystals are characteristic for the trophozite stage on the life cycle of the parasite, hemozoin actually occurs in all *Plasmodium* erythrocyte stages.[56] This is important to note, since ring stage parasites circulate freely in blood, while later stages attach to tissue capillaries, which removes them from circulation. Thus, malaria diagnosis via the detection of hemozoin in peripheral blood samples is feasible.[57] Methods such as laser desorption mass spectrometry[57,58], paramagnetism detection[59], raman spectroscopy[60], formation of nano-bubbles after a laser pulse[61, 62], polarization microscopy[63,64] or magnetically induced dichroism[65] have been used to detect hemozoin. However, these methods have some drawbacks, such as the complex instrumentation needed for their signal readout and a sensitivity which is not high enough to detect low levels of parasitemia.

New detection methods for hemozoin are therefore of great interest. They should be able to detect very low amounts of hemozoin, rely on simple optical readout mechanisms that could be observable with a naked eye or with simple photodetectors. Moreover, they should involve reagents which are stable in storage, cheap and safe to use.

SUMMARY OF THE INVENTION

In view of the above, the problems of the prior art are solved by the diagnostic methods of the invention that allow detection and quantification of biomarkers, such as proteins and metabolites of parasites, for example hemoglobin, hemozoin, heme, and hematin, at low levels of concentration. In an important embodiment, the methods are based on atom transfer radical polymerization carried out above a lower critical solution temperature of the polymer that leads to precipitation. The biomarker acts as a catalyst of the initiation and polymerization reactions.

An object or embodiment of the invention involves obtaining a biological sample to be tested, for example blood, plasma, red blood cells, urine, etc. and adding the sample to a diagnostic test assay mixture including an ATRP polymerizable monomer, such as a vinyl monomer, and an plurality of ATRP initiators.

Still another object or embodiment of the invention involves the step of purifying the sample prior to addition to the diagnostic test assay mixture. Depending on the sample to be tested, the step may or may not be performed. For example, the preliminary step is required to purify hemozoin, hematin, heme or hemozoin-containing parasite from hemoglobin prior to addition to the diagnostic test assay mixture.

A further object or embodiment includes the step of obtaining a diagnostic test assay mixture comprising an ATRP polymerization monomer, such as N-isopropyl acrylamide (NIPAM), ATRP initiators, such as 2-hydroxyethyl 2-bromoisobutyrate (HEBIB), a reducing agent, such as sodium ascorbate, a reaction medium such as one or more of water, plasma, biological sample, buffer and an organic solvent, for example dimethylformamide (DMF).

Still another object or embodiment of the present invention involves performing the polymerization reaction at a temperature at or above the LCST of poly(N-isopropyl acrylamide) (PNIPAM) (32° C.) and preferably at 37° C.

An additional object or embodiment includes the step of providing an initiator to the diagnostic test assay mixture in order to start polymerization of the ATRP-polymerizable monomer, such as a vinyl monomer. HEBIB is utilized as a suitable initiator in one preferred embodiment.

A further object or embodiment of the present invention involves tracking the polymerization by the rate of turbidity formation. In some embodiments, the turbidity formation is recorded as an extinction measurement at 600 nm and 380 nm. The maximum rate of turbidity formation is then correlated to the concentration of the biomarker which can be correlated to the concentration thereof in a biological sample and/or to the stage of the disease.

In yet a further object or embodiment of the present invention, the polymerization is tracked by an end-point measurement, such as turbidity at a point in time after initiation of polymerization or time to reach a certain turbidity after initiation. The measurement is then correlated to the concentration of the biomarker in the biological sample.

The methods of the present invention allow for detection of the biomarker hemoglobin which advantageously, as compared to the prior art, utilizes a procedure that is free of cyanides, has very high sensitivity, and also offers excellent correlation between concentration of Hb and read-out.

The methods of the present invention allow for detection of the biomarker hemozoin for malaria which advantageously, as compared to the prior art, utilizes a procedure that is low priced, uses environmentally benign reagents, has objective read-out in comparison to microscopy, and no need for complex equipment to perform the experiment. The method is quantitative and very sensitive, which allows one to follow the evolution of a patient and avoid overtreatment. It is also possible that the method to diagnose non-symptomatic malaria patents, having very low levels of parasitemia, who need to be treated to achieve eradication in endemic areas, as this population acts as a reservoir for vector infection.

In view of the above, a diagnostic method for the detection of a biomarker in a biological sample is disclosed, comprising the steps of combining at least one and preferably a plurality of initiators, a plurality of monomers, and a biological sample containing a biomarker that serves as a catalyst for a polymerization reaction, at or above a lower critical solution temperature (LCST) whereby a polymer formed by the monomers is precipitable; determining a rate of turbidity formation; and determining a concentration of the biomarker in the biological sample based on the rate of turbidity formation.

In a further aspect, a diagnostic method for the detection of a biomarker in a biological sample is disclosed comprising the steps of: A) combining initiators, a plurality of monomers, and a biological sample containing a biomarker that serves as a catalyst for polymerization reaction, at or above a lower critical solution temperature (LCST) whereby a polymer formed by the monomers is precipitable; B) determining turbidity at i) a point in time after initiation of polymerization or ii) a time to reach a certain turbidity after the initiation, or both i) and ii), and C) determining a concentration of the biomarker in the biological sample based on the determination made in step B.

Still another aspect of the present invention is a diagnostic test kit, comprising a first container comprising a plurality of atom transfer radical polymerization (ATRP) initiators; a second container comprising a plurality of ATRP polymerizable monomers that are able to form a polymer exhibiting a lower critical solution temperature (LCST) at or above which the polymer precipitates, and a plurality of reducing agents.

BRIEF DESCRIPTION OF THE DRAWINGS

The invention will be better understood and other features and advantages will become apparent by reading the detailed description of the invention, taken together with the drawings, wherein.

DETAILED DESCRIPTION OF THE INVENTION

Figure 1:
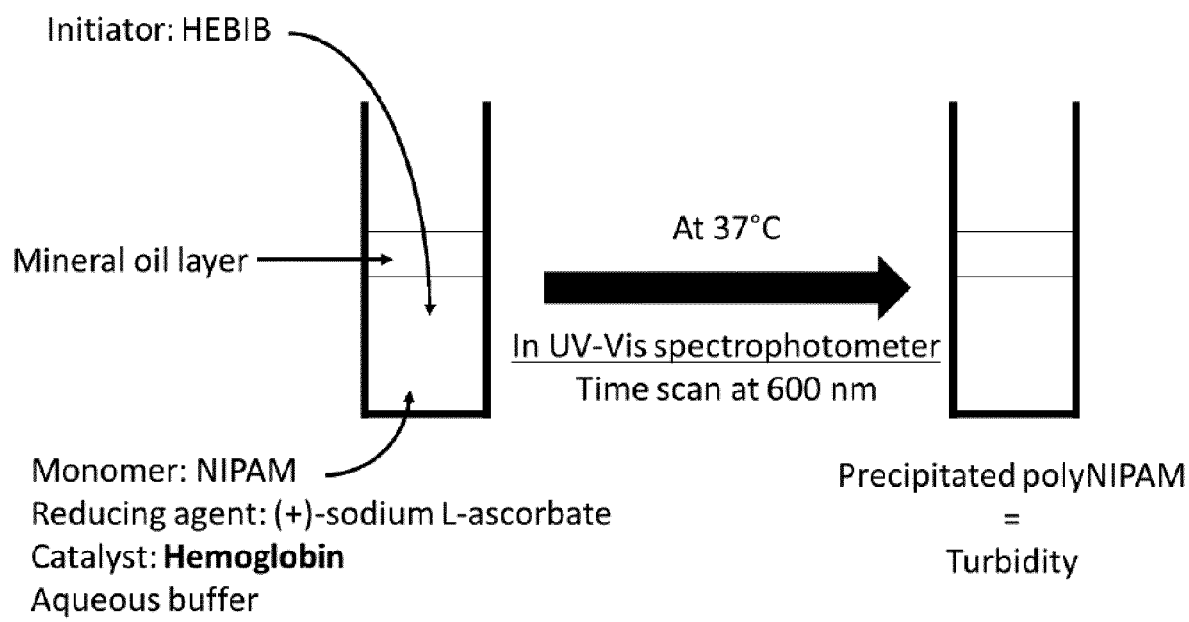
FIG. 1 illustrates a general scheme for one embodiment of an experimental setup for a diagnostic method of the invention wherein the catalyst is hemoglobin.

In this specification, all numbers disclosed herein designate a set value, individually, in one embodiment, regardless of whether the word "about" or "approximate" or the like is used in connection therewith. In addition, when the term such as "about" or "approximate" is used in conjunction with a value, the numerical range may also vary, for example by 1%, 2%, 5%, or more in various other, independent, embodiments.

Diagnostic methods suitable for detection and quantification of blood related diseases or conditions are disclosed herein along with testing kits that can be utilized at a point-of-care location in the field. The methods utilize biomarkers as catalysts in an ATRP reaction performed above a LCST of a polymer, which allows the polymerization to be tracked by rate of turbidity formation.

Biological Sample

The methods require a sample of the biological sample to be analyzed. Depending on the biomarker to be analyzed, the biological sample or body fluid can be for example blood, sometimes considered full blood; red blood cells; plasma; cerebrospinal fluid, feces, a biopsy sample and urine. The biological sample can be collected as known to those of ordinary skill in the art, such as for example by a simple blood draw or urine collection.

In some embodiments of the invention, a preliminary step is required to purify the biomarker or a biomarker-containing parasite from the biological sample. For example, in one embodiment a preliminary step is required to purify hemozoin or a hemozoin-containing parasite from hemoglobin. The resulting solution can then be added to the diagnostic test assay mixture.

For example, hemozoin can be purified in one embodiment as follows: *Plasmodium* sp. containing blood is treated with a solution of saponin. Saponin selectively lyses the RBCs membrane and leaves the parasites intact. The resulting suspension is centrifuged, obtaining in the pellet cell membranes in addition to the malaria parasites which contain hemozoin. This pellet is suspended in NaOH of suitable molar concentration, preferably of 0.4M NaOH, and added to the test solution. Alternatively, *Plasmodium* sp. containing blood is treated with a solution of saponin. The resulting suspension is filtered, eliminating hemoglobin and keeping the cell membranes and the hemozoin containing parasites as the filtrate. As another option, blood is suspended in a solution of NaOH of suitable molar concentration. The suspension is added to an organic solvent which selectively dissolves hemozoin and precipitates hemoglobin. The supernatant is used for the polymerization test.

In one embodiment, hemozoin can be purified through hypotonic lysing. A sample of blood containing malaria parasites is exposed to distilled water. The lysate is then purified using a column that is capable of selectively eluting the hemozoin.

In one embodiment, a MACS column from Miltenyi Biotec is used, which permits all contents of the lysate to pass through a magnetic field. The content of the lysate elutes through the column except for the hemozoin which stays magnetically attached or otherwise held within the column. Once the hemozoin is purified the magnetic field is removed and the hemozoin eluted therefrom.

An additional purification procedure is set forth in the following document: P. Parroche, F. N. Lauw, N. Goutagny, E. Latz, B. G. Monks, A. Visintin, K. A. Halmen, M. Lamphier, M. Olivier and D. C. Bartholomeu, *Proceedings of the National Academy of Sciences,* 2007, 104, 1919-1924.

An additional purification procedure is set forth in the following document: J. M. Combrinck, K. Y. Fong, L. Gibhard, P. J. Smith, D. W. Wright, T. J. Egan, *Malaria Journal,* 2015, 14, 253.

Monomers

The diagnostic test assay mixture also includes a plurality of monomers that are polymerized during a polymerization reaction. In a preferred embodiment, the same type of monomers are used, such that a homopolymer is formed, e.g. PNIPAM. In other embodiments, two or more different types of monomers may be utilized. Examples of suitable monomers include, but are not limited to, N-isopropylacrylamide (NIPAM), N-n-propylacrylamide, N-cyclopropylacrylamide, N,N-diethylacrylamide, N—(N'-isobutylcarbamido)propyl methacrylamide, N—(N'-ethylcarbamido)propyl methacrylamide, N-(1-hydroxymethyl)propylmethacrylamide, [N-(2,2-dimethyl-1,3-dioxolane)methyl] acrylamide, N-(2-methoxy-1,3-dioxan-5-yl) methacrylamide, N-(2,2-dimethyl-1,3-dioxan-5-yl) methacrylamide, N-(2,2-di-methyl-1,3-dioxan-5-yl) acrylamide, N-vinylisobutyramide, N-vinyl-n-butyramide, N-acryloyl-N'-propylpiperazine, N-vinylcaprolactam, N-vinylpyrrolidone, N-(2-methacryloyloxyethyl) pyrrolidone, N-ethylpyrrolidine methacrylate, N-acryloylpyrrolidine, dimethylaminoethyl methacrylate, 2-(2-methoxyethoxy)ethyl methacrylate, 2-[2-(2-methoxyethoxy)ethoxy]ethyl methacrylate, poly(ethylene glycol) acrylate, poly(ethylene glycol) methacrylate, oligo(ethylene glycol) acrylate, oligo(ethylene glycol) methacrylate, endo,exo-bicyclo[2.2.1]hept-5-ene-2,3-dicarboxylic acid bis[2-[2-(2-ethoxyethoxy)ethoxy]ethyl] ester, 4-vinylbenzyl methoxytetrakis(oxyethylene)ether, bis((ethoxyethoxy)ethoxy)phosphazene, bis(2,3-bis(2-methoxyethoxy)propanoxy) phosphazene], methyl vinyl ether, 2-(2-ethoxy)ethoxyethyl vinyl ether, 2-methoxyethyl vinyl ether, 2-methoxyethyl vinyl ether, ethoxyethyl glycidal ether, N-acryloyl-I-proline methyl ester, N-acryloyl-L-aline N'-methylamide, 2-hydroxypropylacrylate and crosslinkers such as N,N'-methylenebisacrylamide. One requirement of the monomers is that they are able to be polymerized under ATRP conditions. Another requirement is that the polymer formed by the monomers has an LCST at or above which the polymer is precipitable. In one embodiment, the polymers derived by the monomers of the present invention have an LCST at or above 4° C. to about 100° C., and preferably at or above 32° C. to about 45° C. and most preferably at 33° C. PNIPAM is a preferred temperature-responsive polymer of the present invention. The monomers of the polymers have to be soluble in the reaction medium of the polymerization. The monomer is used generally at a concentration of about 0.1 mg/mL to saturation and preferably at a concentration of about 100 mg/mL.

Reaction Medium

The diagnostic test assay mixture also includes a reaction medium in which the polymerization is performed. The type of reaction media depends on the type of monomer and/or catalyst utilized. In some embodiments the reaction medium can be water or the biological sample itself, such as plasma, urine or full blood.

In another embodiment the reaction medium can be a mixture of two or more of a biological sample, such as plasma, urine or blood, and an aqueous buffer.

In some embodiments a solvent that is miscible with water is utilized, such as dimethylformamide (DMF). The amount of reaction medium should be sufficient in order to conduct the polymerization reaction.

In some embodiments, a buffer is used, containing buffer salts and other salts such as sodium chloride. The buffer pH is set, such as, but not limited to, between 1 to 14, preferably 2 to 8, and most preferably, but not limited to pH 6.

Reducing Agent

The diagnostic test assay mixture also includes a reducing agent in a preferred embodiment. The reducing agent can be any suitable compound that is able to lose an electron during the polymerization reaction. Examples of suitable reducing agents include, but are not limited to, ascorbic acid, sodium ascorbate, formic acid, oxalic acid, galic acid, tartaric acid, quinic acid, malic acid, malonic acid, citric acid, fumaric acid, acetic acid, caffeic acid, lactic acid and sodium dithionite. In a preferred embodiment, the reducing agent is soluble in the reaction medium. The reducing agent is used generally at a concentration of about 0.1 mg/mL to about 100 mg/mL, and preferably at a concentration of about 17.51 mg/mL.

Initiator

The diagnostic methods of the present invention also utilize an initiator that initiates the polymerization reaction. Preferably a plurality of initiators are used. The term "initiator used herein refers to one or more initiators that can be the same or a mixture of two or more different initiators. Therefore, in a preferred embodiment of the present invention, the desired components of the diagnostic test assay mixture are combined except for the initiator, with the initiator being added at a time that it is desired for the polymerization reaction to begin. The initiator is soluble in the reaction medium. Any suitable ATRP initiator known to those of ordinary skill in the art can be utilized. Examples of suitable initiators include, but are not limited to 2-azidoethyl 2-bromoisobutyrate; bis[2-(2'-bromoisobutyryloxy)ethyl] disulfide; bis[2-(2-bromoisobutyryloxy)undecyl] disulfide; 2-bromoisobutanoic acid N-hydroxysuccinimide ester; 2-bromoisobutyric anhydride; α-bromoisobutyryl bromide; 2-(2-bromoisobutyryloxy)ethyl methacrylate; tert-butyl α-bromoisobutyrate; 3-butynyl 2-bromoisobutyrate; dipentaerythritol hexakis(2-bromoisobutyrate); dodecyl 2-bromoisobutyrate; ethyl α-bromoisobutyrate; ethylene bis(2-bromoisobutyrate); 2-hydroxyethyl 2-bromoisobutyrate; 1-(DL-1,2-Isopropylideneglyceryl) 2-bromoisobutyrate; methyl α-bromoisobutyrate; 2-(4-morpholino)ethyl 2-bromoisobutyrate; octadecyl 2-bromoisobutyrate; pentaerythritol tetrakis(2-bromoisobutyrate); 1-(phthalimidomethyl) 2-bromoisobutyrate; poly(ethylene glycol) bis(2-bromoisobutyrate); poly(ethylene glycol) bis(2-bromoisobutyrate); poly(ethylene glycol) bis(2-bromoisobutyrate); poly(ethylene glycol) methyl ether 2-bromoisobutyrate; poly(ethylene glycol) methyl ether 2-bromoisobutyrate; poly (ethylene glycol) methyl ether 2-bromoisobutyrate; poly (ethylene glycol) methyl ether 2-bromoisobutyrate; propargyl 2-bromoisobutyrate; 1,1,1-tris(2-bromoisobutyryloxymethyl)ethane; 10-undecenyl 2-bromoisobutyrate.

In a preferred embodiment, 2-hydroxyethyl 2-bromoisobutyrate (HEBIB) is utilized as an initiator. This initiator is soluble in the reaction medium. Concentration range: about 0.1 mg/mL to about 50 mg/mL, preferred concentration: about 3.97 mg/mL.

Polymerization

In order to measure the maximum rate of turbidity formation, the polymerization is monitored, preferably by time-resolved extinction measurements, such as a with an UV-vis spectrophotometer. In additional embodiments of the invention, the polymerization is tracked from initiation of polymerization and the turbidity is measured after a predetermined period of time. In still other embodiments, the time from initiation until a certain level of turbidity has been reached is measured and recorded. These values are utilized to determine the concentration of the biomarker in the biological sample based on the measurement. In addition to the monitoring by a spectrophotometer as described above, other optical means can be utilized, for example, but not limited to, devices that measure light scattering or even the human eye. In a preferred embodiment, the rate of turbidity formation is measured at one or more wavelengths between 200 and 900 nm, preferably but not limited to 600 nm or 380 nm. As mentioned hereinabove, the polymerization reaction is conducted at a temperature at or above the LCST of the polymer formed from the monomer. About 37° C. is preferred in one embodiment. Absorbance at a desired wavelength can be recorded at various time intervals in order to determine the maximum rate of turbidity. The maximum rate of turbidity formation is then correlated to a concentration of the biomarker. A calibration curve is constructed by reporting the maximum rate of turbidity formation at different concentration. Samples with unknown concentration will have their concentration determined by reporting their maximum turbidity rate to the calibration curve. Determining a concentration of the biomarker in a biological sample based on an end-point measurement such as turbidity after a certain period of time or the time until a certain level of turbidity has been reached can also utilize a calibration curve. The calibration curves are constructed by defining the end-point measurements for samples with known concentrations. Samples with unknown concentrations have their concentration determined by correlating their measurement value with the calibration curve. In all cases, the calibration curve data correlating an observed measurement with a known concentration can be codified in a processor or other computer-like device Experimental Section Hemoglobin Detection The following paragraphs describe methods for diagnosing different kinds of anemia and the presence of hemoglobin in urine. The detection of hemoglobin is achieved by the combination of biocatalytic ATRP and a precipitation polymerization.

Blood was obtained from blood-bank human donors and subjected to ATRP conditions to polymerize NIPAM. The reactions were conducted at a temperature of 37° C., above the lower critical solution temperature (LCST) of poly(N-isopropyl acrylamide) (PNIPAM), and the rate of turbidity formation was monitored as extinction measurements at 600 nm. The maximum rate of turbidity formation was then correlated to the concentration of hemoglobin. An assay with a detection limit as low as 3 µg mL$^{-1}$ (48.55 pM) of hemoglobin per cuvette was developed. This assay could be used as a qualitative test to determine the presence of hemoglobin in certain body fluids, or the quantification of hemoglobin in a variety of biological samples, determining the presence of certain blood-borne diseases such as genetic sickle cell anemia or malaria.

Materials

Human blood samples (from healthy blood donors) were routinely obtained on a weekly basis from the blood donation and transfusion service (Bern, Switzerland). In accordance with the bio-safety level 2 certification, all individuals working with human blood were immunized with Hepatitis B and conducted their research in coherence with the specific standards of use and disposal necessary for this bio-safety level. All other chemicals were purchased from Sigma-Aldrich and were used as received except for N-isopropyl acrylamide (NIPAM) which was recrystallized from hexane.

ACK lysis buffer: 155 mM $NH_4Cl$, 10 mM $NaHCO_3$ and 0.1 mM EDTA in MilliQ water.

PBS buffer: 137 mM NaCl, 2.7 mM. 10 $Na_2HPO_4$, $KH_2PO_4$ 1.8 mM in 800 mL MilliQ water. The pH was adjusted to 7.4 with 1M HCl and volume was adjusted to 1 L.

0.1 M Sodium phosphate buffer pH 6 with saline salts: 1 M $Na_2HPO_4$, and 1 M $NaH_2PO_4$ solutions in MilliQ water were made. 120 mL of the $Na_2HPO_4$ were measured and then 880 mL of the $NaH_2PO_4$ were added. Solutes were added to a total concentration of 137 mM NaCl and 2.7 mM KCl.

Drabkin stock solution: 0.61 mM $K_3Fe(CN)_6$, 0.77 mM KCN and 1.03 mM $KH_2PO_4$ in MilliQ water.

Methods

Blood Plasma Isolation

Blood plasma was isolated from full blood which was centrifuged at 1000×g for 20 minutes at 25° C. The supernatant was then passed into new falcon tubes and then submitted to centrifugation during 8 minutes at 500×g to eliminate any possible cells. The supernatant was once again isolated from the pellets.

Red Blood Cell (RBC) Isolation From Plasma, Buffy Coat and Platelets

RBCs were isolated using an established protocol, see W. Gao, C.-M. J. Hu, R. H. Fang, B. T. Luk, J. Su and I. Zhang, Advanced Materials, 2013, 25, 3549-3553. After full blood centrifugation (at 4° C., 800×g for 5 minutes), the RBC fraction was isolated and then aliquoted (5 mL) in 50 mL Falcon tubes. PBS was added to a final volume of 50 mL and the re-suspended RBCs were centrifuged for 2 minutes at 500×g at 25° C. The supernatant was discarded and the process was repeated three more times. The resulting pellets were then re-suspended in PBS to a final volume of 45 mL and stored at −20° C., inducing partial hemolysis.

RBC Lysis and Isolation of Human Hemoglobin From RBC Membranes

The previous partially hemolysed samples were incubated for 30 minutes with 50 mL ACK lysis buffer. They were then centrifuged at 4696×g during 10 minutes at 1° C. (Thermo Scientific, Heraeus Megafuge 16R, TX-400×400 mL Swinging Bucket Rotor) to obtain a pellet of RBC membranes. The supernatant was then concentrated by spin diafiltration using a Macrosep Advance centrifugal device with a molecular weight cut-off of 10 KDa to a volume of 5 mL. Then, PBS buffer was added to the complete volume of the tube and the sample concentrated again by centrifugation. The process was repeated twice to wash away the ACK lysis buffer.

Finally, the sample was concentrated to a volume of 4 mL. The fresh solution was used for further experiments within 24 h.

Human Hemoglobin Concentration Determination

The hemoglobin concentration was determined using the Drabkin colorimetric assay[7]. To 1 mL of the Drabkin stock solution, 1 µl, 2 µl, 5 µl, 10 µl and 20 µl of the human hemoglobin stock solution were added in 5 different PMMA UV/Vis cuvettes of 1 mL, vortexed and incubated for 20 minutes. UV-vis measurements were then performed at 540 nm. Taking into account the dilutions and the molar absorptivity of hemoglobin (11000 | mol$^{-1}$ cm$^{-1}$)[7], an average of the measurements was obtained giving a final concentration value.

Sample Preparation for Polymerization Test

Polymerizations in 0.1 M sodium phosphate buffer pH 6 with saline salts with purified human hemoglobin: In a typical experiment, NIPAM (1.429 g, 12.63 mmol) and (+)-sodium L-ascorbate (250 mg, 1.26 mmol) were weighted in a glass vial and 10 of 0.1 M sodium phosphate buffer (pH 6.0) were added to form a stock solution which was further used for the polymerization reactions. 0.7 mL of this solution were aliquoted into disposable semi-micro poly(methyl methacrylate) cuvettes (path length: 1 cm)mL. These solutions were then spiked with different volumes of the human hemoglobin solution to obtain different final hemoglobin concentrations and then filled to a final volume of 0.95 mL with the 0.1M phosphate buffer pH 6. The solutions were gently vortexed avoiding spilling of the cuvette and were sealed with 0.5 mL mineral oil. The cuvettes were immediately placed in a thermostatted six-cell holder at 37° C. (Julabo 6 thermostat) of an UV/Vis spectrophotometer (Specord 50 plus, Analytik Jena). After 2 minutes of thermal equilibration, 50 µl of a 1.77 µM HEBIB solution in DMF was added to the aqueous phase and the absorbance at 600 nm was recorded every 30.6 seconds (integration time 1 s, slow time scan) during 2 h (FIG. 1).

Polymerizations in 0.1 M sodium phosphate buffer pH 6 with saline salts with isolated RBCs: The same procedure was applied as for the previous polymerizations, substituting the addition of purified human hemoglobin by a suspension of isolated RBCs in PBS buffer.

Polymerizations in 0.1 M sodium phosphate buffer pH 6 with saline salts with full blood: The same procedure was applied as in 1, substituting the addition of purified human hemoglobin by the addition of full human blood.

Polymerizations in 0.1 M sodium phosphate buffer pH 6 with saline salts 10 v/v % hemoglobin containing human blood plasma: The same stock solution of monomer with (+)-sodium L-ascorbate as in 1 was employed. 0.7 mL of this stock solution were aliquoted into PMMA cuvettes followed by the addition of 0.1 mL of isolated human blood plasma. Then, a series of defined volumes of purified human hemoglobin were spiked simulating the diagnosis of haemolytic anemia. 0.1 M sodium phosphate buffer (pH 6) with saline salts was added to a final volume of 0.95 mL. Finally, the same treatment as in 1 was applied to the cuvettes.

Polymerizations in 0.1M sodium phosphate buffer pH 6 with saline salts with 10 v/v % hemoglobin containing human urine: The same procedure was applied as in 4, substituting the addition of human blood plasma by human urine.

Results and Discussion

Blood is a complex fluid. It is the only tissue formed by a liquid matrix, which is the blood plasma. The blood plasma is formed by the solution of organic small molecules, inorganic salts and plasma proteins such as albumin. Moreover, blood contains several types of cells which can be generally described as blood platelets, white blood cells (WBCs) and red blood cells (RBCs). It is therefore important to determine which molecules are responsible for the catalytic activity of the blood, and what components of the blood may influence in the kinetics of these reactions.

Figure 2:
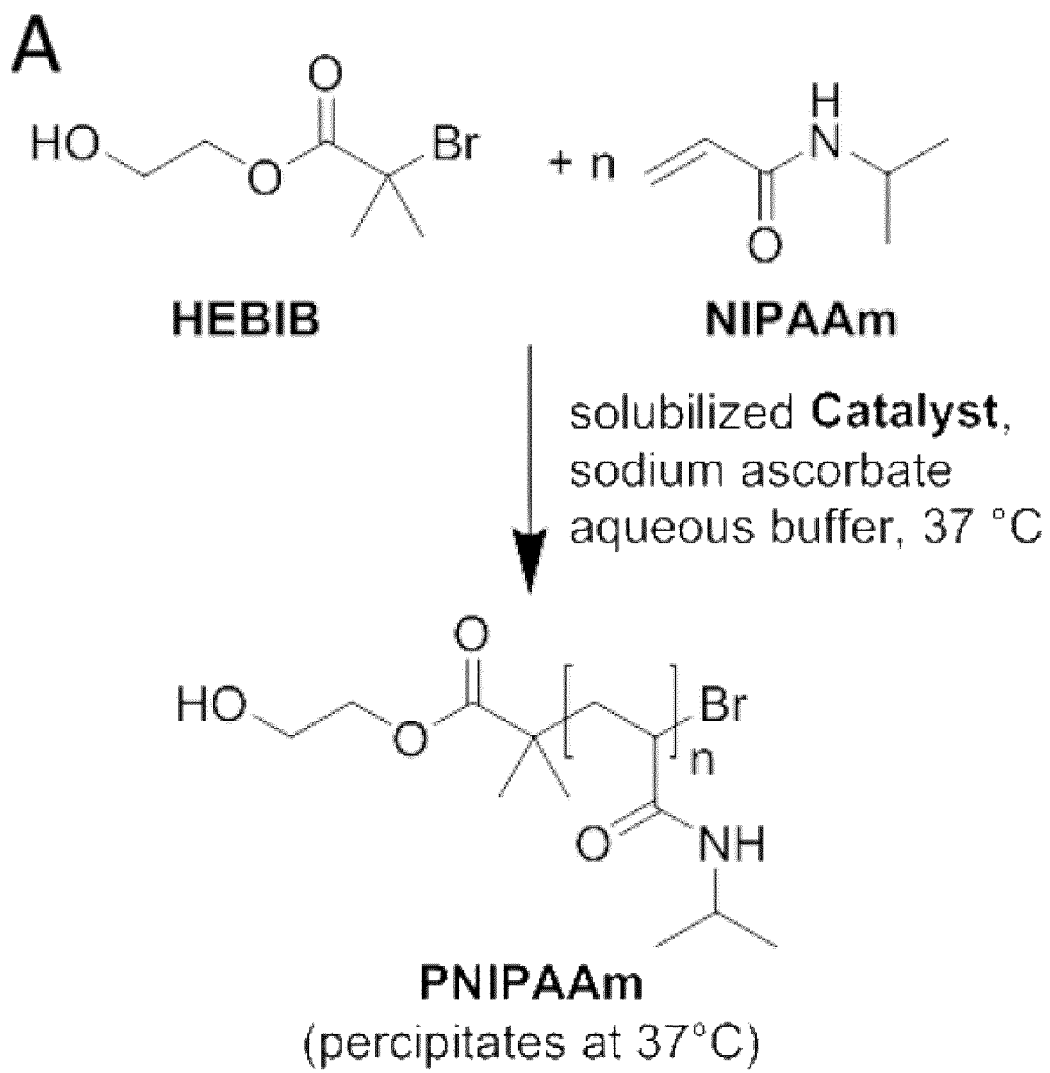
FIG. 2 illustrates hemoglobin-quantification assay based on hemozoin-catalyzed polymerization of NIPAM at 37° C. wherein A) illustrates a reaction scheme of the polymerization, and B) is a graph of turbidity formation (measured as extinction at 600 nm) during a polymerization, caused by the precipitation of the temperature responsive polymer PNIPAM. After an initial lag, the turbidity increases linearly with time. The slope of this section is the readout of the assay.
Figure 2:
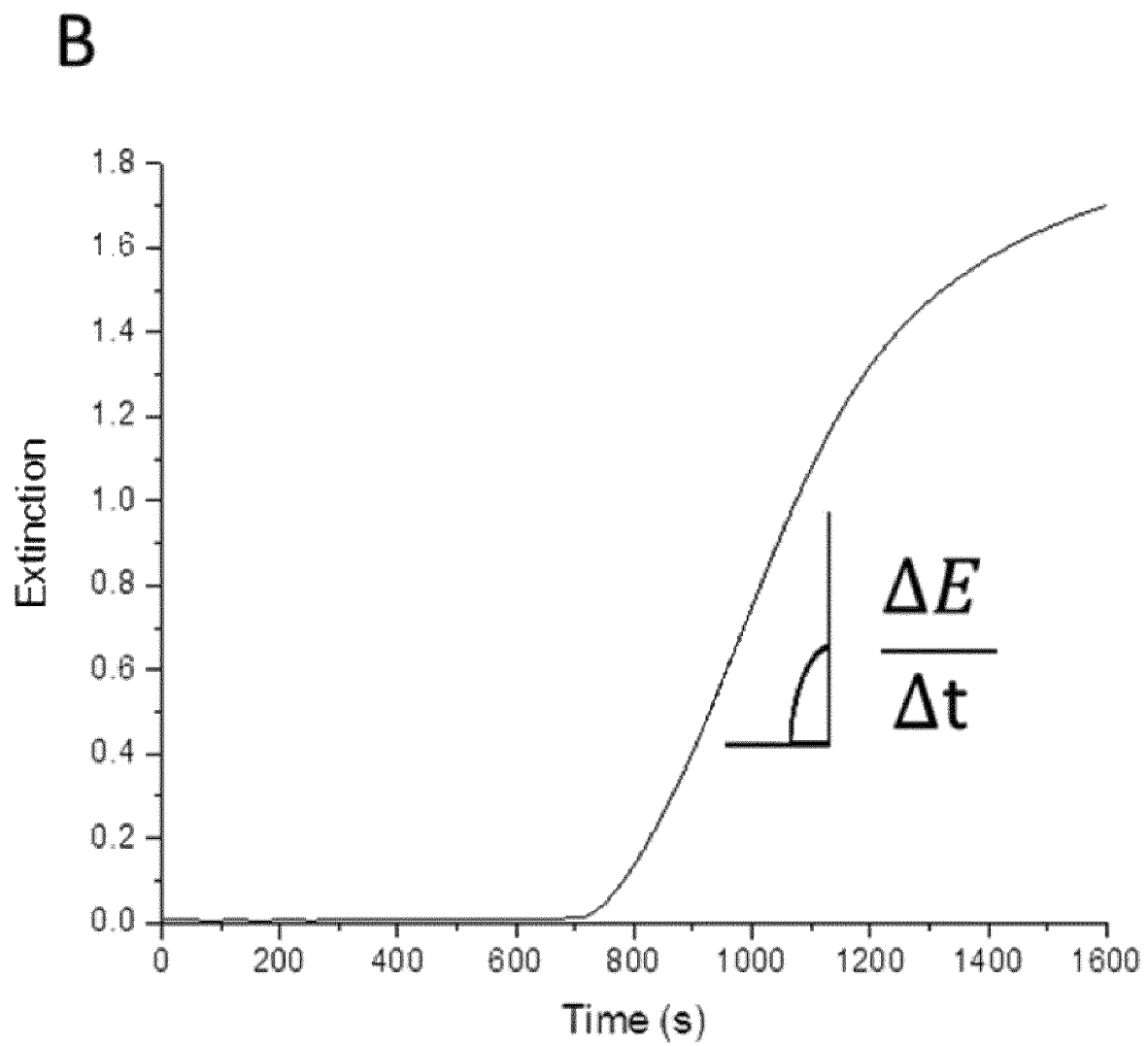
Figure 3:
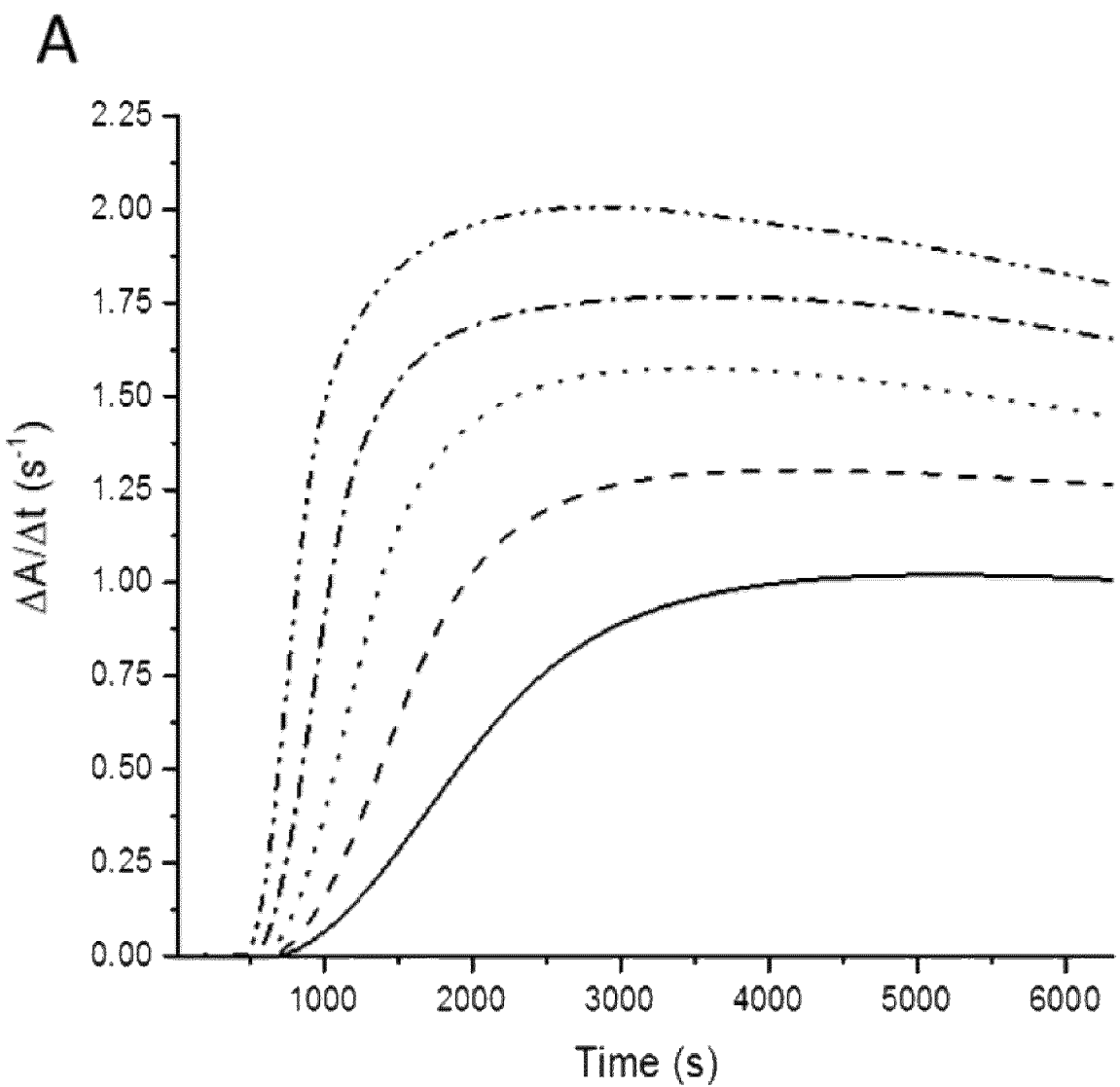
FIG. 3 illustrates A) turbidity measurements at different concentrations of purified human hemoglobin. Samples used for the calibration curve at concentrations of 50 μg mL$^{-1}$ (line, dot, dot), 25 μg mL$^{-1}$ (line, dot), 12.5 μg mL$^{-1}$ (dots), 6.25 μg mL$^{-1}$ (discontinuous lines), 3.13 μg mL$^{-1}$ (continuous line) per cuvette. B) Dose response curve between hemoglobin concentration and increase in extinction over time. A linear fit in the near-to-linear region of the curves was employed to correlate the rate of turbidity formation with the concentration of catalyst. C) Turbidity measurements at different concentrations of human hemoglobin in isolated RBCs. 0.6 mg mL$^{-1}$ (short discontinuous lines), 0.5 mg mL$^{-1}$ (line, dot, dot), 0.4 mg mL$^{-1}$ (line, dot), 0.3 mg mL$^{-1}$ (dots), 0.2 mg mL$^{-1}$ (discontinuous lines), 0.1 mg mL$^{-1}$ (continuous line) per cuvette. D) Correlation curve between hemoglobin concentration in isolated RBCs and increase in extinction over time. A linear fit in the near-to-linear region of the curves was employed to correlate the rate of turbidity formation with the concentration.
Figure 3:
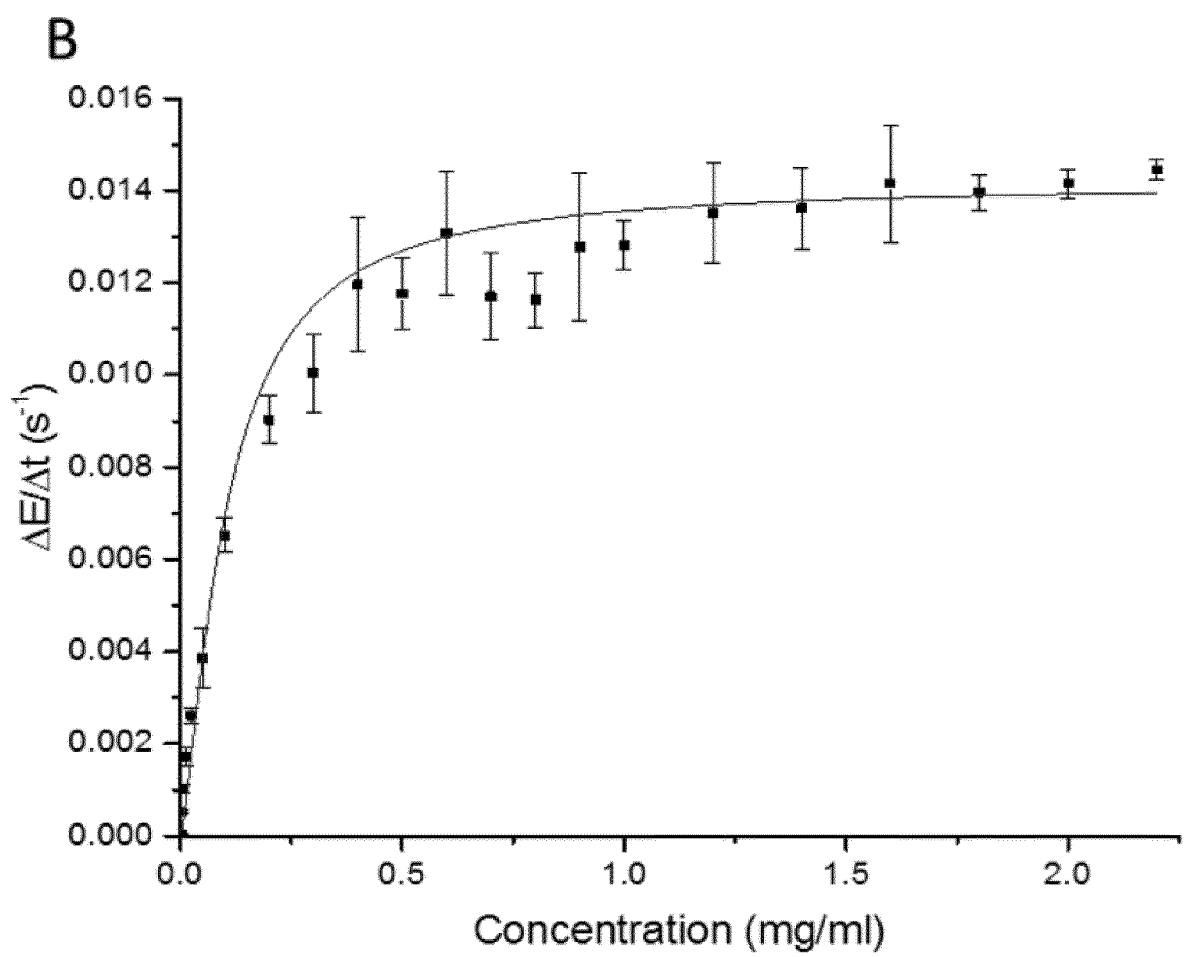
Figure 3:
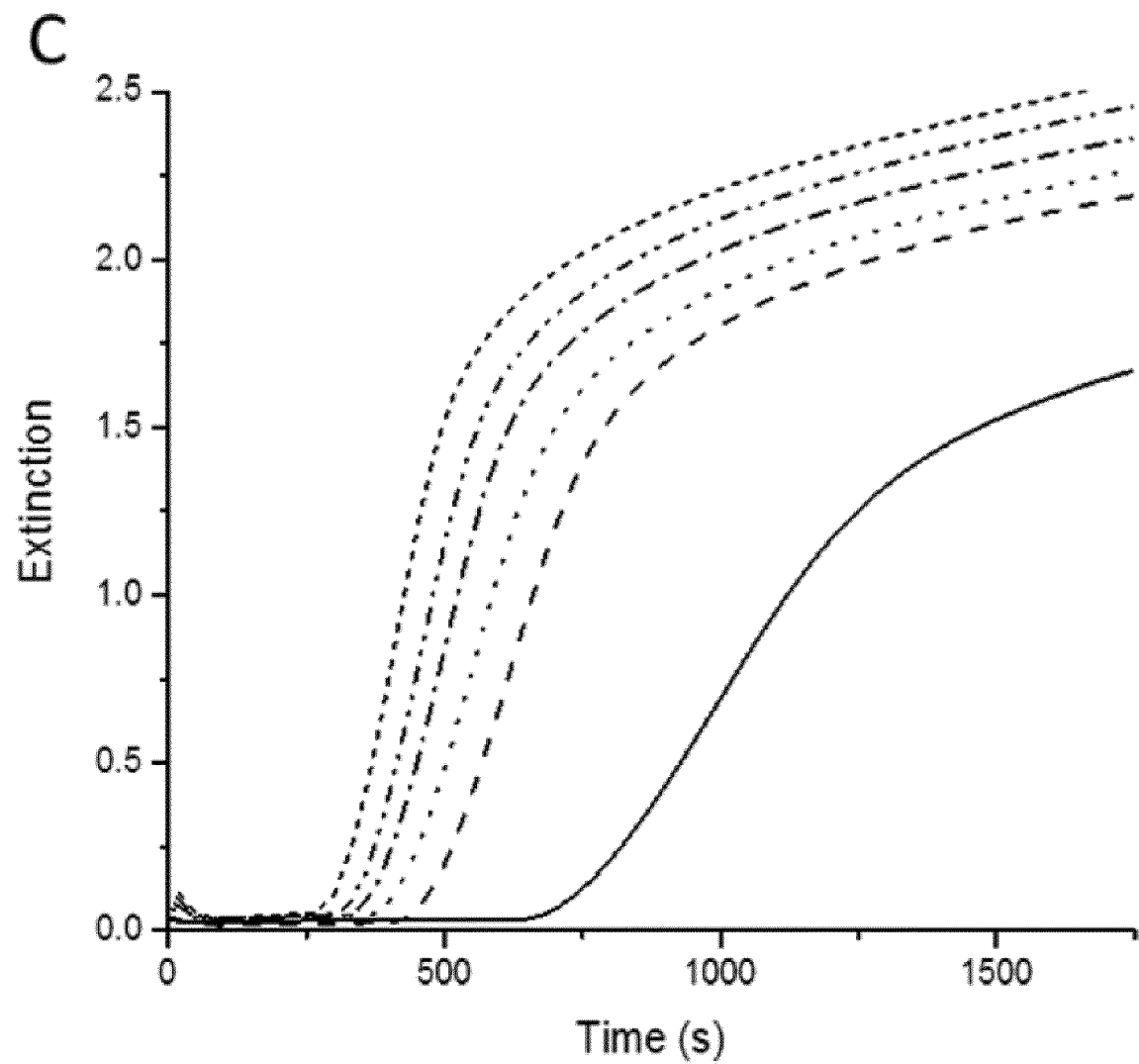
Figure 3:
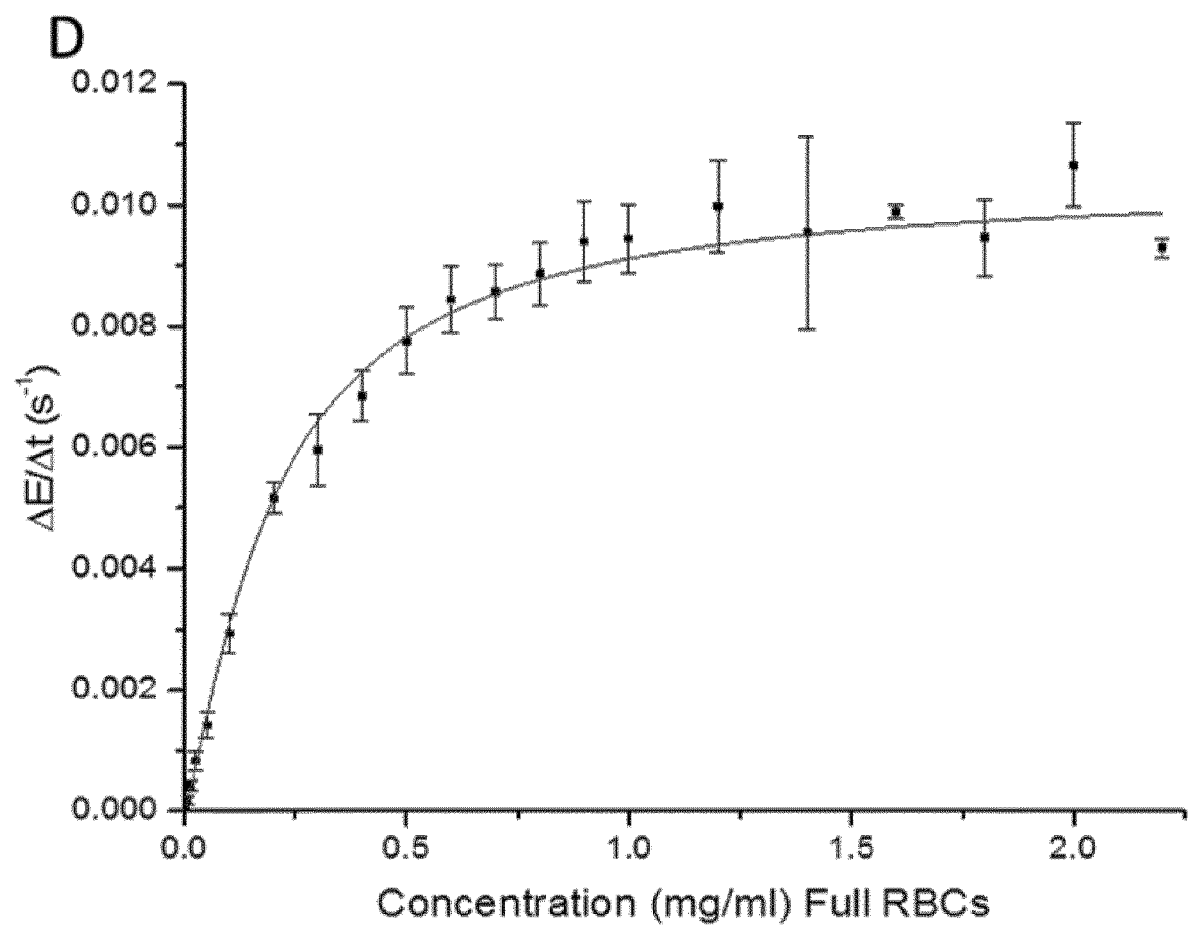

0.1 M sodium phosphate buffer (pH 6) solutions with saline salts containing the monomer NIPAM and sodium ascorbate were thermostatted in cuvettes for spectroscopy at 37° C. These solutions were spiked with known amounts of purified human hemoglobin and sealed with a layer of mineral oil from atmospheric oxygen. Finally, the tests were started with the addition of the initiator 2-hydroxyethyl bromoisobutyrate (HEBIB) into the aqueous phase. The formation of turbidity was monitored as an extinction measurement at 600 nm. The concentrations of the reactants were adjusted for the best correlation between the concentration of the catalyst and the readout of the test. Throughout the polymerization reactions, an initial lag phase in which there was no increase in extinction was observed. This phase was followed by a near-to-linear increase in extinction ($\Delta E/\Delta t$) as a result of turbidity formation. After a certain time, the increase in extinction became slower reaching a plateau for the reaction. The slope of this near-to-linear region of the curve correlated to the concentration of human hemoglobin. The software Origin was used to obtain the maximum rate of turbidity formation by applying a linear fit to the near-to-linear region of the curve (FIG. 2A). A calibration curve was obtained using different concentrations of hemoglobin (FIG. 3B).

Higher concentrations of hemoglobin correlated with faster increases in optical density, shorter lag phases and higher turbidities at the endpoint of the reactions. A calibration curve could be obtained for the assay by plotting $\Delta E/\Delta t$ against the concentration of human hemoglobin. Hemoglobin concentrations down to 3.13 µg mL$^{-1}$ (48.55 pM) per cuvette could be detected. Above a threshold of approx. 0.5 mg mL$^1$ hemoglobin the assay has reached saturation and does not distinguish between different protein concentrations. Therefore, to use these calibration curves for the determination of hemoglobin concentration, full blood should be diluted to a concentration between 0 and 0.5 mg mL$^1$ of hemoglobin per cuvette to give a reliable read-out. In the case of the determination of hemoglobin in urine or blood plasma, as low concentrations are normally found, see D. J. Schaer, P. W. Buehler, A. I. Alayash, J. D. Belcher and G. M. Vercellotti, Hemolysis and free hemoglobin revisited: exploring hemoglobin and hemin scavengers as a novel class of therapeutic proteins, 2013, no dilution is needed.

This experiment served as a simple system to understand the kinetics of the reaction catalyzed by hemoglobin. However, the previous system assumed that the all the hemoglobin in blood was free from the confinement of the RBCs. Therefore, the polymerization kinetics with isolated RBCs was studied. An initial slight decay in extinction was observed. This phase was followed by the same stages which were observed for the reactions with purified hemoglobin: a lag phase, a near-to-linear increase in turbidity and a plateau (FIG. 3C). A correlation function between the slope at the near-to-linear region and the concentration of hemoglobin was also achieved (FIG. 3D).

Figure 4:
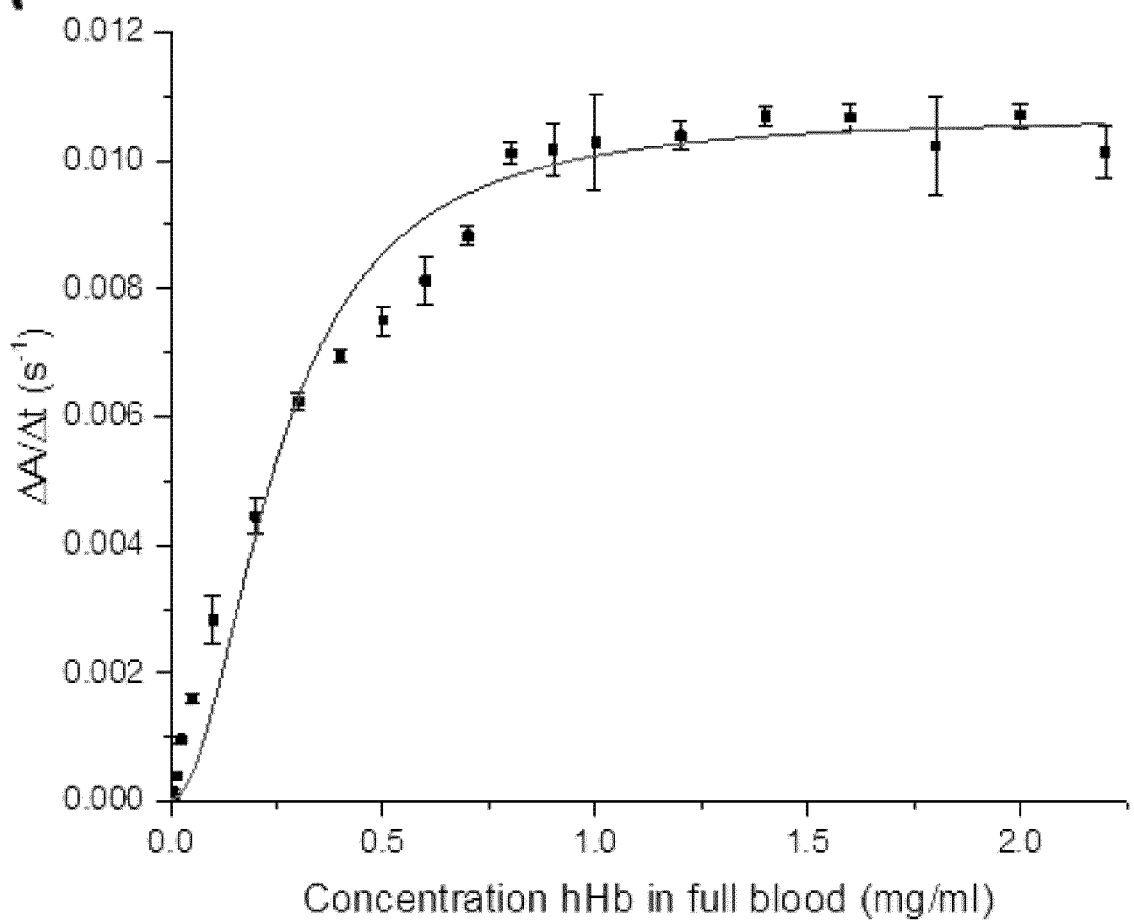
FIG. 4 illustrates correlation functions for different biological samples, A) hemoglobin in full blood, B) hemoglobin in urine, C) hemoglobin in blood plasma.
Figure 4:
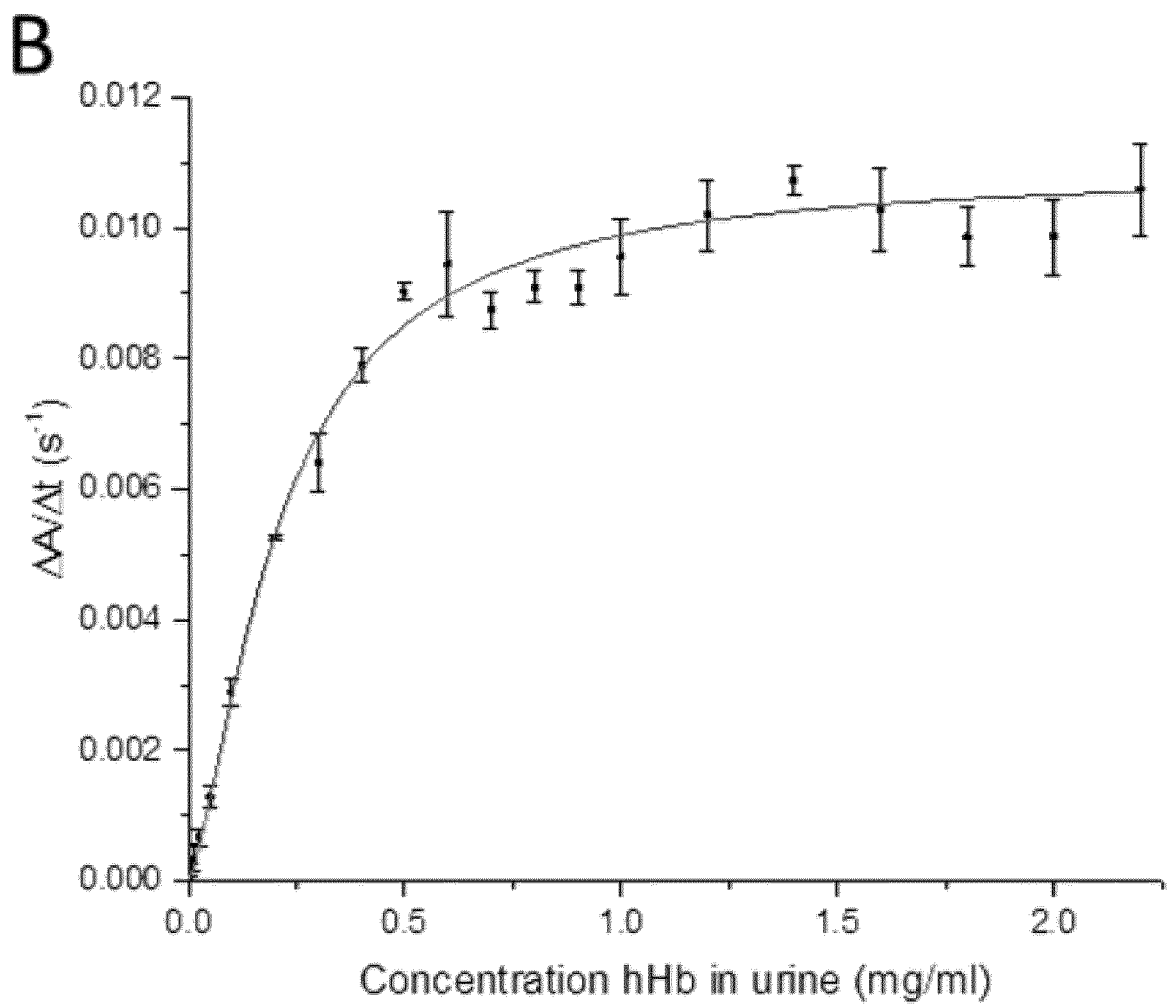
Figure 4:
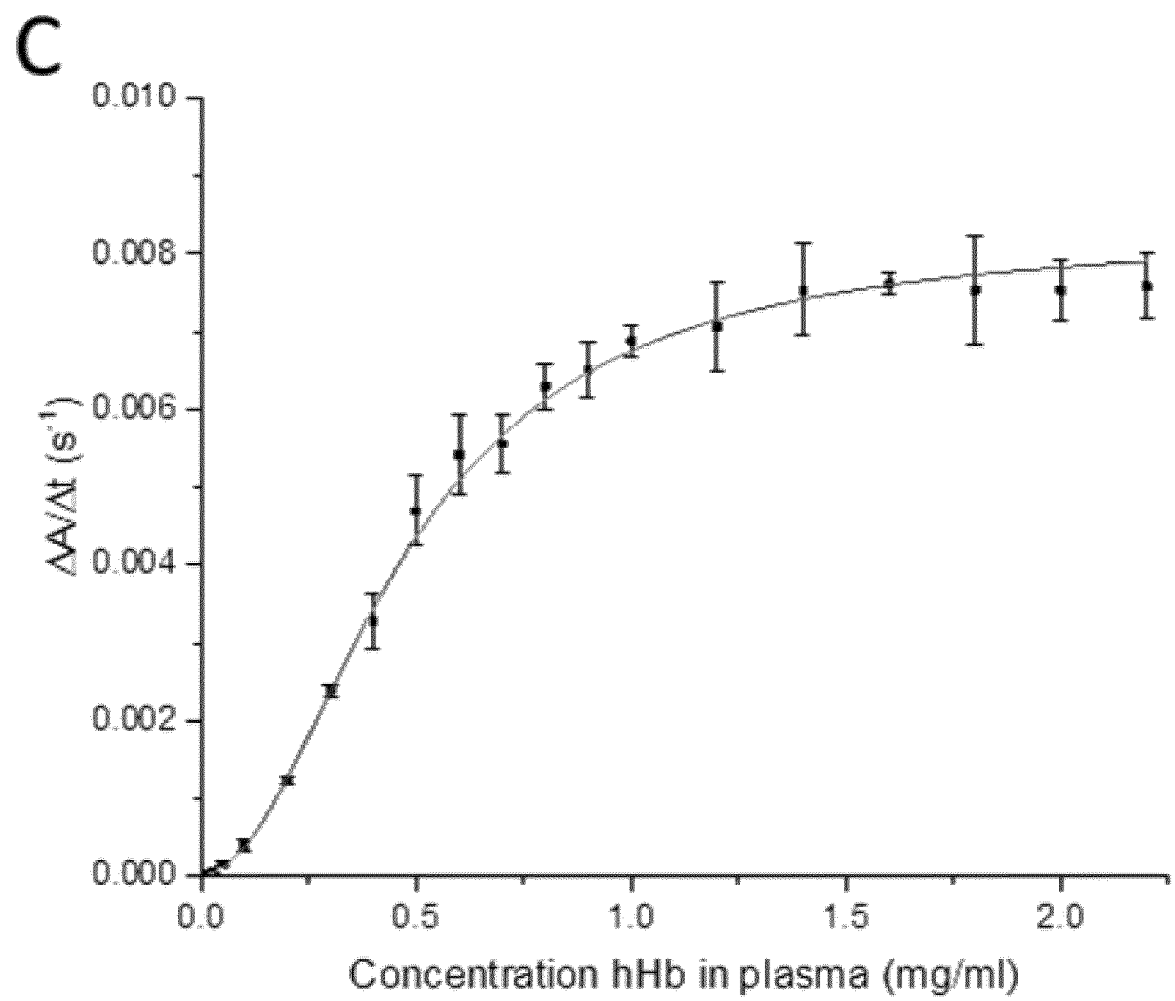
Figure 5:
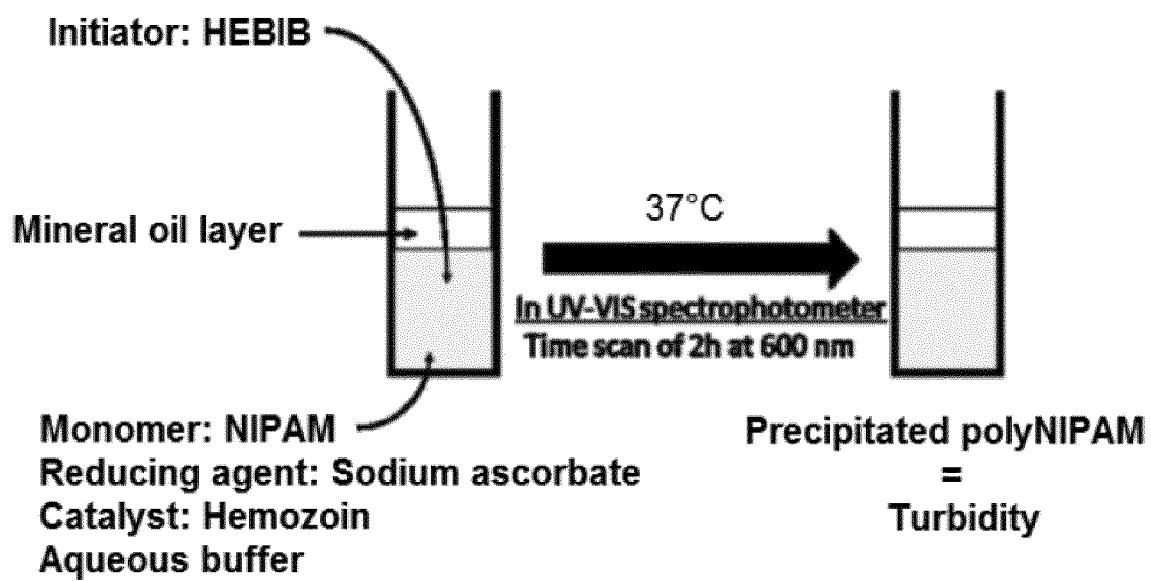
FIG. 5 illustrates a general scheme for one embodiment of an experimental setup for a diagnostic method of the invention wherein the catalyst is hemozoin.

Different calibration curves were obtained for different kinds of biological samples. FIGS. 4A-C show curves for total hemoglobin determination from full blood (FIG. 4A), determination of hemoglobin in urine (FIG. 4B) and quantification of free hemoglobin in human plasma (FIG. 4C). The polymerization reactions with pure hemoglobin appeared to be faster than with isolated RBCs. Moreover, the presence of biological samples such as plasma or urine seemed to have an influence in the polymerization rate. The reactions catalyzed by hemoglobin dissolved in urine had a slower rate of turbidity formation than for pure hemoglobin in buffer. The turbidity formation was slower in blood plasma than in urine.

Malaria Detection

The following content describes a method for the detection of malaria based on the implication of the metabolite or biomarker hemozoin (HZ). This reaction is the combination of a biocatalytic atom transfer radical polymerization and a precipitation polymerization, with hemozoin being the catalyst for the reaction. A correlation function between the quantity of HZ and the maximum rate of turbidity formation throughout the polymerization was obtained, making the test a quantitative method for the detection of malaria. The results presented below show a very sensitive malaria diagnosis method involving highly stable and relatively inexpensive chemicals. The developed test is an inexpensive qualitative method which can be applied at a point of care in the field and used to detect malaria in patients who did not show symptoms and to monitor their treatment with the further goal of avoiding over-treatment. Importantly, the methods of the present invention can be conducted in plain air with the test solution being isolated therefrom by a compound such as mineral oil as shown in the figures.

Purified hemozoin was obtained from *Plasmodium falciparum* cultures and subjected to ATRP conditions to polymerize NIPAM. The measurement was conducted at 37° C., i.e. above the lower critical solution temperature (LCST) of poly(N-isopropyl acrylamide) (PNIPAM), permitting to track the rate of turbidity formation which was recorded as an extinction measurement at 600 nm. The rate of polymerization is then correlated to the quantity of the malaria catalyst which can finally be correlated to the parasitemia.

Materials

Synthetic hemozoin (sHZ) was purchased from Invivo-Gen and was used as received. Natural hemozoin (nHZ) from *Plasmodium falciparum* was obtained from 30 mL of 10% trophozoite late-stage cultures which were then hypotonically lysed and frozen. The lysate was purified using a MACS column (Miltenyi Biotec), which permits to pass all the contents through a magnetic field. All the contents were eluted except for nHZ which stayed magnetically attached. Once the nHZ is purified, the magnetic field was removed and nHZ was eluted, see P. Parroche, F. N. Lauw, N. Goutagny, E. Latz, B. G. Monks, A. Visintin, K. A. Halmen, M. Lamphier, M. Olivier and D. C. Bartholomeu, *Proceedings of the National Academy of Sciences*, 2007, 104, 1919-1924. The hemozoin was then dispersed in 1 mL of MilliQ water.

All other chemicals were purchased from Sigma-Aldrich and were used as received except for N-isopropyl acrylamide (NIPAM) which was recrystallized from hexane.

Methods

Solubilization of Hemozoin

The dispersion of natural hemozoin was centrifuged at 12100×g for 5 minutes and the supernatant was discarded to obtain a pellet which was dried overnight under vacuum at 40° C. A defined quantity of hemozoin was then solubilized in 0.4 M NaOH during 2 h, passing from an insoluble black crystal to a light green solution ("hemozoin stock solution").

NIPAM Polymerizations With Hemozoin as Catalyst 1.429 g (12.63 mmol) of NIPAM were weighted together with 250 mg (1.26 mmol) of (+)-sodium L-ascorbate into a round-bottom flask. Then, 10 mL of sodium phosphate buffer solution (pH 6.0, 0.1 M) were added to obtain a stock solution which was employed for the polymerization reactions. 0.700 mL of this stock solution were pipetted into 1 mL poly(methyl methacrylate) cuvettes. Various volumes of hemozoin solutions in 0.4 M NaOH were added for nHz. For sHz, the volume of catalyst was varied but was then adjusted to a total volume of 0.05 mL of 0.4 M NaOH. The volume of buffer was adjusted to achieve a final volume of 0.950 mL in each cuvette. The solutions were then sealed against ambient oxygen by adding 0.500 mL of mineral oil. The cuvettes were incubated for five minutes in a thermostatted 6 cell changer of a UV/Vis spectrophotometer (Specord 50 Plus, Analytik Jena) at 37° C. Finally, the polymerization was initiated by the addition of 50 µl of a 1.77 µM 2-hydroxyethyl 2-bromoisobutyrate (HEBIB) solution in DMF. The absorbance at 600 nm or at 380 nm was immediately recorded every 30 s with an integration time of 1 s during 2 h. The maximum rate of turbidity formation ($\Delta E/\Delta t$) was calculated from absorbance vs. time plots by the application of a linear fit to the near-to-linear region of the curve. The assays were carried out in triplicate. Mean values and standard deviations are reported. These values were then plotted against the concentration of catalyst to obtain a calibration curve for the polymerization-based hemozoin quantification assay.

Results and Discussion

Difference and Similarity Between Synthetic and Natural Hemozoin

Synthesized β-hematin is considered a chemically and structurally analogue to natural hemozoin (nHZ) and is therefore called synthetic hemozoin (sHZ). The main difference between these two species is that nHZ still contains part of the globine chains from the previously digested hemoglobin and also, a fraction of the lipoproteins which are involved in the process of biocrystallization. This chemical difference translates into different solubility features. Natural hemozoin is not readily soluble in water and needs to be incubated in basic conditions to be solubilized (0.1 M NaOH solutions). After an incubation period, nHZ is totally soluble and can be diluted without any precipitation. sHZ can be obtained as a pure compound that it is readily soluble in 0.1 M NaOH. Thus, sHZ is ideally suited to develop an assay. Furthermore, polymerizations driven in reaction solutions containing sHZ prove that the catalytic activity of hemozoin is due to the heme and not due to amino-acids or lipids which are clustered on the crystals of nHZ.

Polymerization Catalyzed by sHZ

Figure 6:
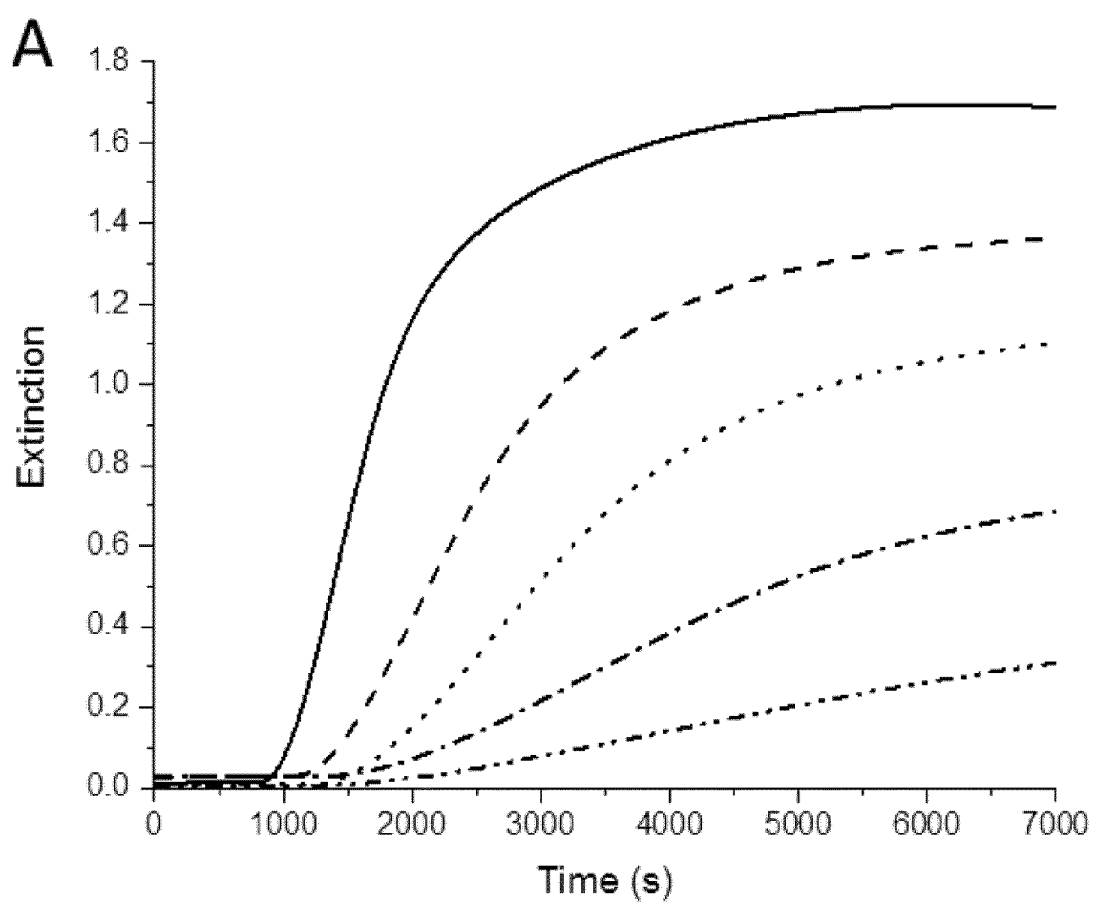
FIG. 6 illustrates A) turbidity measurements at different concentrations of synthetic hemozoin (Shz). 200 ng mL$^{-1}$ (continuous line), 100 ng mL$^{-1}$ (discontinuous lines), 50 ng mL$^{-1}$ (blue), 25 ng mL$^{-1}$ (dots), 10 ng mL$^{-1}$ (line, dot), 5 ng mL$^{-1}$ (line, dot, dot) per cuvette. B) Dose response curve between the concentration of sHZ and the rate of turbidity formation.
Figure 6:
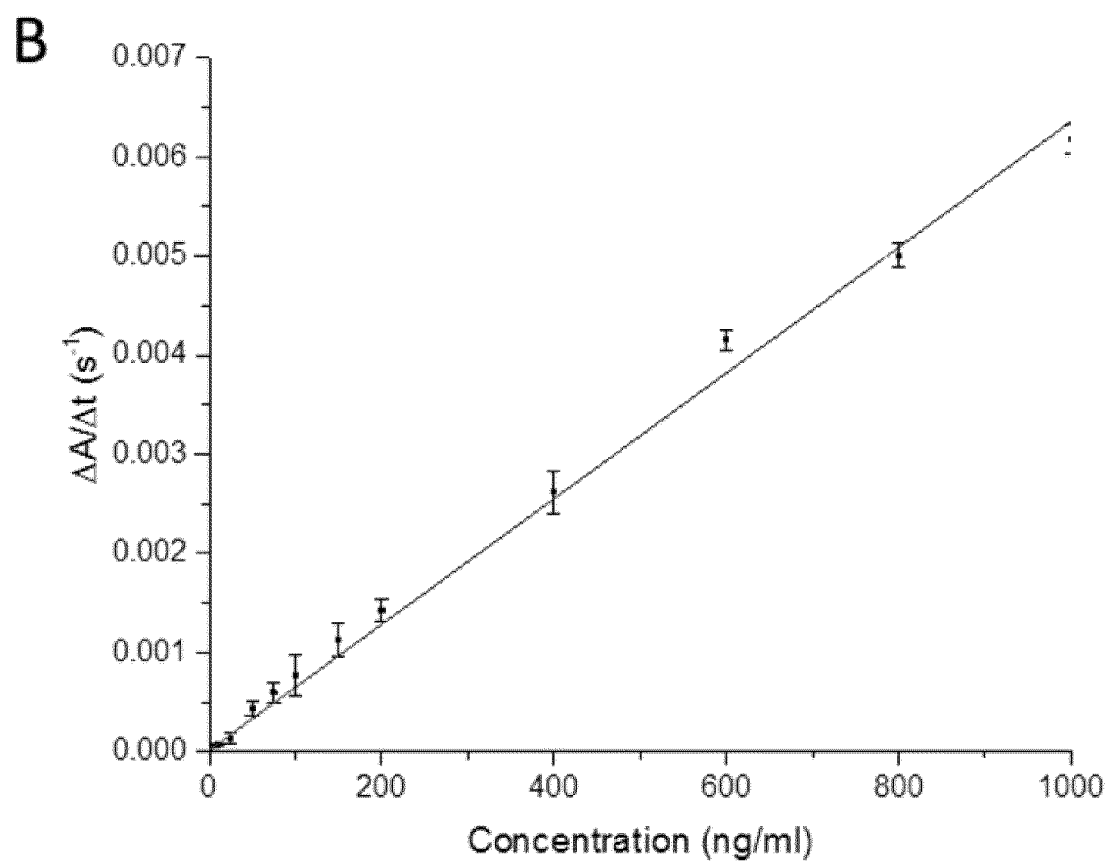

Assay solutions (buffered at pH 6) containing NIPAM and sodium ascorbate were thermostatted in spectroscopic cuvettes to 37° C. and spiked with known concentrations of sHz. Then, the solutions were sealed from air by a layer of mineral oil and the reactions were started by adding the initiator 2-hydroxyethyl bromoisobutyrate (HEBIB) into the aqueous phase. Formation of turbidity at 37° C. was monitored by continuous absorption measurements at 600 nm or at 300 nm. After an initial lag phase, the absorption increased linearly with time. At longer reaction times the formation of turbidity slowed down until the reaction reached a plateau. The slope of this linear part ($\Delta E/\Delta t$) was taken as the quantitative readout of the assay. In order to evaluate the quantitative correlation between hemozoin concentration and optical readout, a series of experiments with various sHz concentrations was carried out (FIG. 6A). A higher hemozoin concentration resulted in a faster increase in optical density, as well as a shorter lag phase and higher turbidity at the end of the reaction. $\Delta E/\Delta t$ was plotted against the hemozoin concentration, resulting in a calibration curve for the assay (FIG. 6B). This biosensing by polymerization can detect as low as 5.41 ng mL$^{-1}$ per cuvette, and the $\Delta E/\Delta t$ is a function of the hemozoin concentration even at these low concentrations.

Spectroscopic Determination of Natural Hemozoin Concentration

In order to prepare a calibration plot for the polymerization-based quantification assay of nHz, NIPAM polymerizations had to be carried out with known amounts of nHz. However, the exact concentration of heme in the nHz samples was not known, since it was prepared from biological samples that contained an unknown amount of non-heme compounds (vide supra). Therefore, the amount of heme present in the samples of nHz was determined by UV-vis spectroscopy, using sHz as the reference. To this end, the extinction coefficient of sHz was determined. A dilution series of sHz in 0.4 M sodium hydroxide was prepared, and UV/vis spectra of the samples were recorded. The absorbance at 388 nm was corrected using a baseline point (900 nm). An extinction coefficient of 35.3594 mL mg$^{-1}$ cm$^{-1}$ was determined from the dilution series according to the Lambert-Beer law. With this parameter the concentration of the nHz stock solution was determined from its UV-vis spectrum.

Polymerization Catalyzed by nHZ

Figure 7:
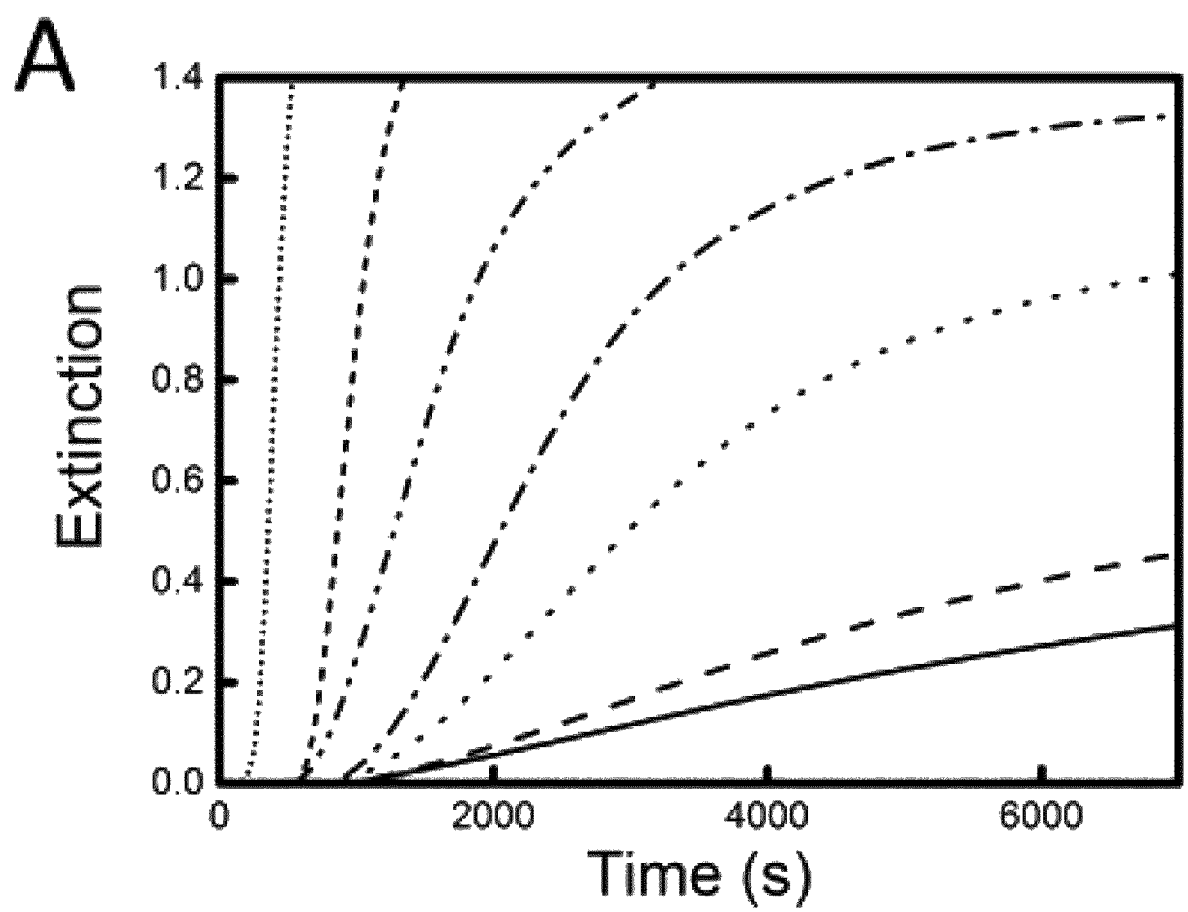
FIG. 7 illustrates A) Natural hemozoin-quantification assay based on hemozoin-catalyzed polymerization of NIPAM at 37° C. and recorded at 600 nm. 10 ng mL$^{-1}$ (solid), 25 ng mL$^{-1}$ (dash), 50 ng mL$^{-1}$ (dot), 100 ng mL$^{-1}$ (Dash dot), 200 ng mL$^{-1}$ (Dash dot dot), 400 μg mL$^{-1}$ (short dash), 1000 ng (short dot) per cuvette. B) Dose response curve for the quantification of natural hemozoin. The readout of the assay scales with the concentration of hemozoin in test samples.
Figure 7:
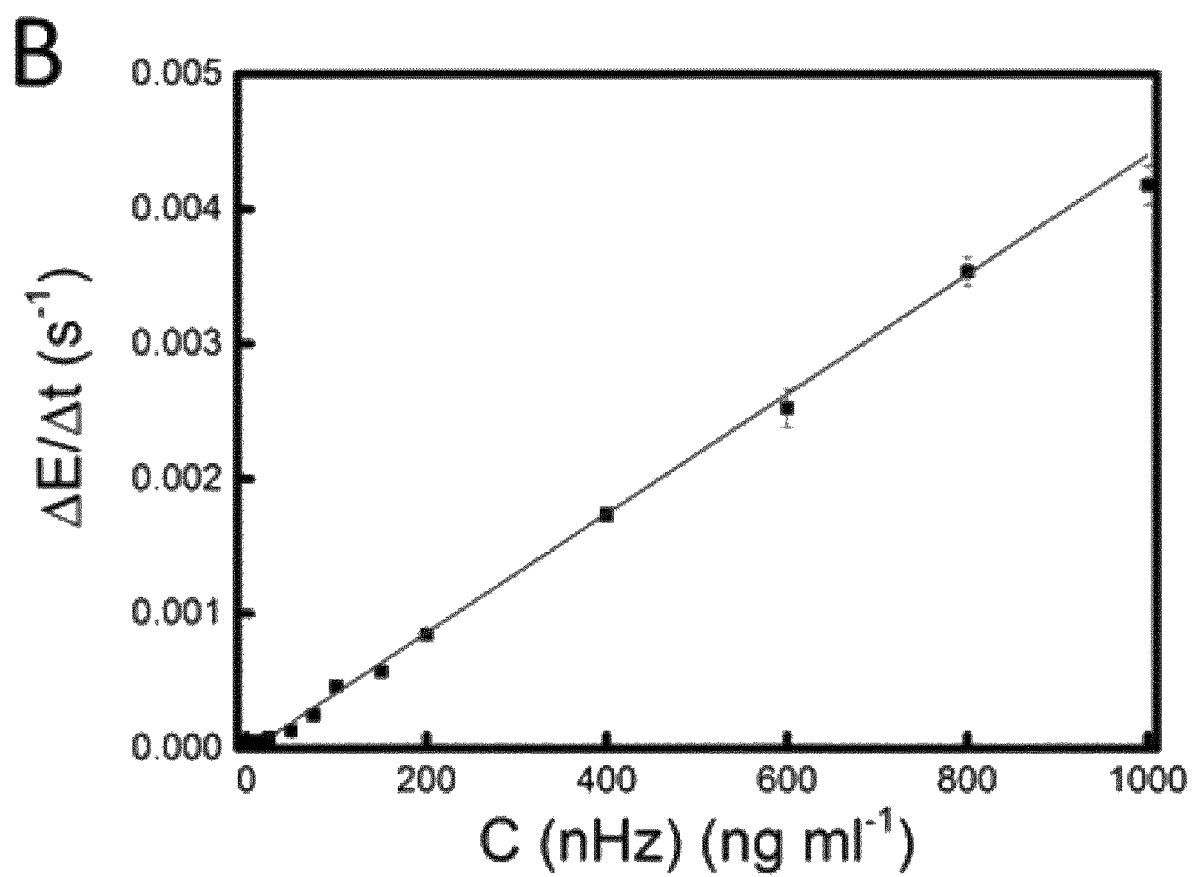
Figure 8:
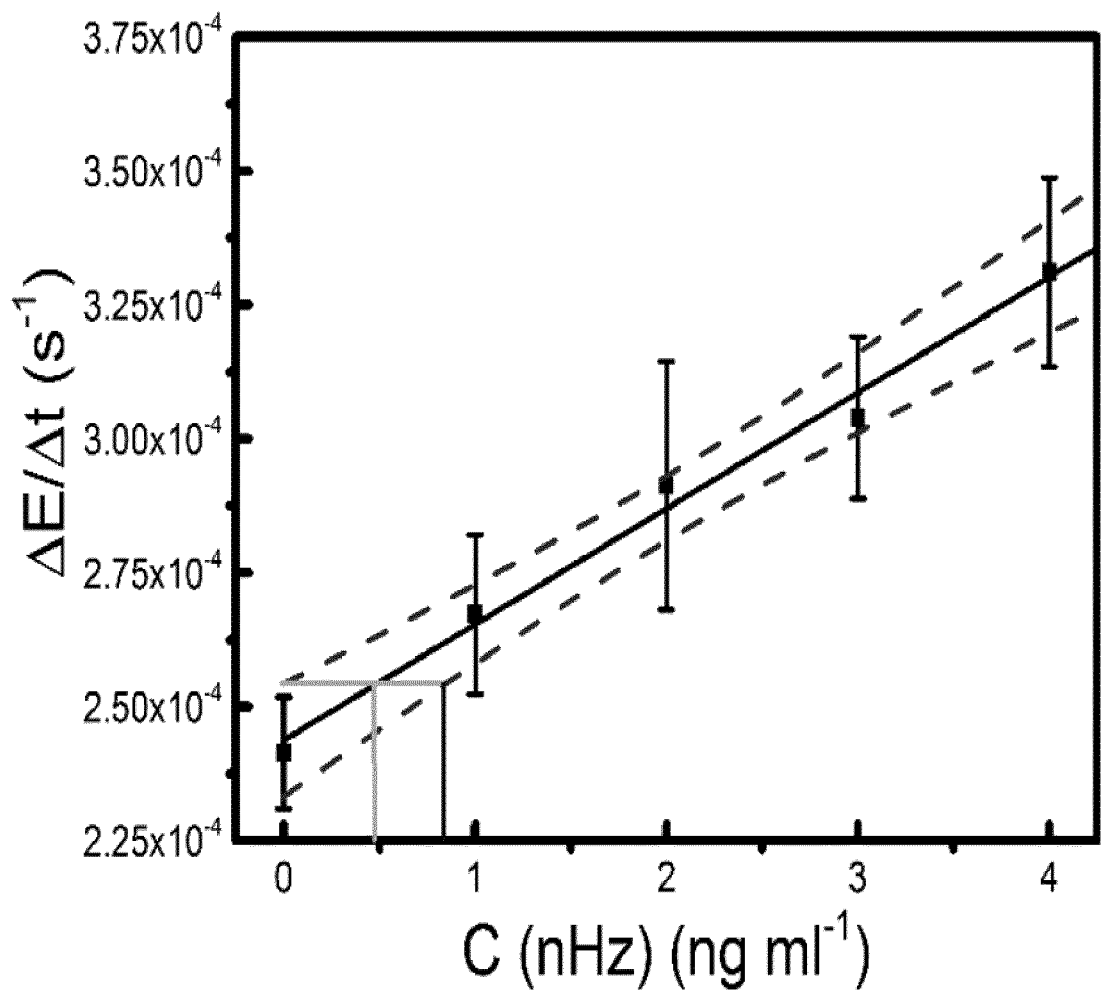
FIG. 8 illustrates the dose response of natural hemozoin (nHz) based on hemozoin-catalyzed polymerization of NIPAM at 37° C. and recorded at 380 nm.

Several precipitation polymerization of NIPAM were carried out with nHz in analogy to those described above for sHz (FIG. 7A). The concentration of nHz was varied between 3.12 µg mL$^{-1}$ and 5.41 ng mL$^{-1}$ per cuvette when measurements were carried out at 600 nm and between 5 to 1 ng mL$^{-1}$ for measurements at 380 nm by adding defined volumes of nHz stock solution to the reaction mixtures. After a lag phase the solutions became turbid. The plots of optical density at 600 nm vs. reaction time were similar to those observed for polymerizations catalyzed by sHz. This result confirms our initial hypothesis that the catalysis of NIPAM polymerization is due to the heme contained in nHZ and not due to the clustered lipids and amino acids. The rate of turbidity formation increased with increasing nHz concentration, which allowed obtaining a calibration curve for the assay that scales $\Delta E/\Delta t$ to the concentration of nHz (FIG. 7B). It shows a linear correlation between signal and hemozoin concentration from 314 ng mL$^{-1}$ to at least 3.12 µg mL$^{-1}$ (the highest concentration that was tested) per cuvette. Below 314 ng mL$^{-1}$ the calibration curve is flatter, but also linear. A detection limit of 5.41 ng mL$^{-1}$ per cuvette at 600 nm and as low as 0.85 ng mL$^{-1}$ per cuvette at 380 nm which corresponds to 1.4 parasites/µL was determined.

The assay can be carried out in a multitude of reaction vessels, including but not limited to spectrophotometric cuvettes, glass capillaries and mutli-well plates.

If the assay is going to be used in the field, it has to be stable in the relatively hot conditions encountered during transport and storage in tropical or subtropical countries. Therefore, we investigated the stability of all reagents in ageing experiments over a period of two months at 50° C. $^{1}$H-NMR spectra before and after this extended exposure to elevated temperatures did not reveal any differences, i.e. the compounds did not appear to degrade and were stable. This hints towards a long shelf-life of the assay even at high temperatures, which represents an important advantage over current MRDTs or primers for PCR.

While in accordance with the patent statutes the best mode and preferred embodiment have been set forth, the scope of the invention is not limited thereto, but rather by the scope of the attached claims.

REFERENCES

1. Worldwide prevalece of anaemia 1993-2005. Geneva: World Health Organization, 2008.
2. The global prevalence of anaemia in 2011. Geneva: World Health Organization, 2015.
3. D. Das, C. Chakraborty, B. Mitra, A. Maiti and A. Ray, Journal of microscopy, 2013, 249, 136-149.
4. P. Nestel and H. Taylor, Anemia detection methods in low-resource settings: a manual for health workers, Program for Appropriate Technology in Health, 1997.
5. V. Han, K. Serrano and D. V. Devine, Vox Sanguinis, 2010, 98, 116-123.
6. P. Balasubramaniam and A. Malathi, Comparative study of hemoglobin estimated by Drabkin's and Sahli's methods, 1992.
7. J. P. Acker, I. M. Croteau and Q.-L. Yi, Clinica Chimica Acta, 2012, 413, 1746-1752.
8. M. D. John H. Tinker and M. D. John D. Michenfelder, Anesthesiology, 1976, 45, 340-352.
9. K. Maiese, I. Boniece, D. DeMeo and J. Wagner, The Journal of Neuroscience, 1993, 13, 3034-3040.
10. V. Shah, B. Shah and G. Puranik, Evaluation of non cyanide methods for hemoglobin estimation, 2011.
11. A. Barati, M. Shamsipur and H. Abdollahi, Biosensors and Bioelectronics, 2015, 71, 470-475.
12. E. Keohane, L. Smith and J. Walenga, Rodak's Hematology: Clinical Principles and Applications, Elsevier Health Sciences, 2015.
13. M. Harboe, Scandinavian journal of clinical and laboratory investigation, 1959, 11, 66-70.
14. I. Oshiro, T. Takenaka and J. Maeda, Clinical biochemistry, 1982, 15, 83-88.
15. H. von Schenck, M. Falkensson and B. Lundberg, Clinical Chemistry, 1986, 32, 526-529.
16. Q. Cao, S. Wang, Z. Feng, C. You, L. Kong, X. Weng and Y. Ruan, Sensors and Actuators B: Chemical, 2015, 208, 50-53.
17. G. Kalaiyarasan, A. V. N. Kumar, C. Sivakumar and J. Joseph, Sensors and Actuators B: Chemical, 2015, 209, 883-888.
18. F. Morgner, A. Lecointre, L. J. Charbonniere and H.-G. Lohmannsroben, Physical Chemistry Chemical Physics, 2015, 17, 1740-1745.
19. S. Pang, S. Liu and X. Su, Talanta, 2014, 118, 118-122.
20. H. J. Zo, J. N. Wilson and J. S. Park, Dyes and Pigments, 2014, 101, 38-42.
21. E. Matysiak, M. Donten, A. Kowalczyk, M. Bystrzejewski, I. P. Grudzinski and A. M. Nowicka, Biosensors and Bioelectronics, 2015, 64, 554-559.
22. Z. Wang, F. Li, J. Xia, L. Xia, F. Zhang, S. Bi, G. Shi, Y. Xia, J. Liu, Y. Li and L. Xia, Biosensors and Bioelectronics, 2014, 61, 391-396.
23. R. Zhang, S. Xu, J. Luo and X. Liu, Microchimica Acta, 2014, 182, 175-183.
24. Y. Sun, H. Du, Y. Lan, W. Wang, Y. Liang, C. Feng and M. Yang, Biosensors and Bioelectronics, 2016, 77, 894-900.
25. S. E. H. Marosek, Journal of Forensic Research, 2013, 2013.
26. R. Li, Q. Jiang, H. Cheng, G. Zhang, M. Zhen, D. Chen, J. Ge, L. Mao, C. Wang and C. Shu, Analyst, 2014, 139, 1993-1999.
27. N. Pourreza and H. Golmohammadi, RSC Advances, 2015, 5, 1712-1717.
28. Z. S. Traore, S. M. Shah and X. Su, Luminescence, 2013, 28, 56-62.

29. X. Lou, P. He, G. O. Okelo and L. He, *Analytical and bioanalytical chemistry*, 2006, 386, 525-531.
30. Y. Wu, W. Wei and S. Liu, *Accounts of chemical research*, 2012, 45, 1441-1450.
31. K. H. Malinowska and M. A. Nash, *Current Opinion in Biotechnology*, 2016, 39, 68-75.
32. T.-Y. Guo, Y.-Q. Xia, G.-J. Hao, B.-H. Zhang, G.-Q. Fu, Z. Yuan, B.-L. He and J. F. Kennedy, *Carbohydrate Polymers*, 2005, 62, 214-221.
33. A. J. GormLey, R. Chapman and M. M. Stevens, *Nano Letters*, 2014, 14, 6368-6373.
34. F. Hollmann and I. W. C. E. Arends, *Polymers*, 2012, 4, 759-793.
35. T. B. Silva, M. Spulber, M. K. Kocik, F. Seidi, H. Charan, M. Rother, S. J. Sigg, K. Renggli, G. Kali and N. Bruns, *Biomacromolecules*, 2013, 14, 2703-2712.
36. S. J. Sigg, F. Seidi, K. Renggli, T. B. Silva, G. Kali and N. Bruns, *Macromolecular rapid communications*, 2011, 32, 1710-1715.
37. A. Simakova, M. Mackenzie, S. E. Averick, S. Park and K. Matyjaszewski, *Angewandte Chemie International Edition*, 2013, 52, 12148-12151.
38. K. Yamashita, K. Yamamoto and J.-i. Kadokawa, *Polymer*, 2013, 54, 1775-1778.
39. *Report* 2014. Geneva: World Health Organization, 2014.
40. I. Harris, W. W. Sharrock, L. M. Bain, K.-A. Gray, A. Bobogare, L. Boaz, K. Lilley, D. Krause, A. Vallely, M.-L. Johnson, M. L. Gatton, G. D. Shanks and Q. Cheng, *Malaria Journal*, 2010, 9, 254-254.
41. T. Hänscheid, *Clinical & Laboratory Haematology*, 1999, 21, 235-245.
42. A. Moody, *Clinical Microbiology Reviews*, 2002, 15, 66-78.
43. M. L. Wilson, *Clinical Infectious Diseases*, 2012, 54, 1637-1641.
44. *Malaria rapid diagnostic test performance. Results of WHO product testing of malaria RDTs: Round* 5 (2013), 2014.
45a. C. K. Murray, R. A. Gasser, A. J. Magill and R. S. Miller, *Clinical Microbiology Reviews*, 2008, 21, 97-110.
45b. McMorrow, M. L., Aidoo, M. & Kachur, S. P. Malaria rapid diagnostic tests in elimination settings—can they find the last parasite? *Clin. Microbiol. Infect.* 17 (2011).
46. L. L. M. Poon, B. W. Y. Wong, E. H. T. Ma, K. H. Chan, L. M. C. Chow, W. Abeyewickreme, N. Tangpukdee, K. Y. Yuen, Y. Guan, S. Looareesuwan and J. S. M. Peiris, *Clinical Chemistry*, 2006, 52, 303-306.
47. V. Desakorn, K. Silamut, B. Angus, D. Sahassananda, K. Chotivanich, P. Suntharasamai, J. Simpson and N. J. White, *Transactions of The Royal Society of Tropical Medicine and Hygiene*, 1997, 91, 479-483.
48. P. F. Mens, H. M. de Bes, P. Sondo, N. Laochan, L. Keereecharoen, A. van Amerongen, J. Flint, J. R. S. Sak, S. Proux, H. Tinto and H. D. F. H. Schallig, *Journal of Clinical Microbiology*, 2012, 50, 3520-3525.
49. N. Hofmann, F. Mwingira, S. Shekalaghe, L. J. Robinson, I. Mueller and I. Felger, *PLoS Medicine*, 2015, 12, e1001788.
50. K. A. Mangold, R. U. Manson, E. S. C. Koay, L. Stephens, M. Regner, R. B. Thomson, L. R. Peterson and K. L. Kaul, *Journal of Clinical Microbiology*, 2005, 43, 2435-2440.
51. P. A. Sigala and D. E. Goldberg, *Annual Review of Microbiology*, 2014, 68, 259-278.
52. M. Olivier, K. Van Den Ham, M. T. Shio, F. A. Kassa and S. Fougeray, *Frontiers in Immunology*, 2014, 5.
53. L. M. Coronado, C. T. Nadovich and C. Spadafora, *Biochim. Biophys. Acta, Gen. Subj.*, 2014, 1840, 2032-2041.
54. C. Biot, W. Castro, C. Y. Botte and M. Navarro, *Dalton Transactions*, 2012, 41, 6335-6349.
55. P. F. Scholl, A. K. Tripathi and D. J. Sullivan, in *Malaria: Drugs, Disease and Post-genomic Biology*, eds. R. W. Compans, M. D. Cooper, T. Honjo, H. Koprowski, F. Melchers, M. B. A. Oldstone, S. Olsnes, M. Potter, P. K. Vogt, H. Wagner, D. Sullivan and S. Krishna, Springer Berlin Heidelberg, 2005, vol. 295, ch. 12, pp. 293-324.
56. D. J. Sullivan, in *Biopolymers: Miscellaneous biopolymers, biodegradation of synthetic polymers*, eds. S. Matsumura and A. Steinbüchel, Wiley-VCH Verlag GmbH & Co. KGaA, Weinheim, Germany, 2005, vol. 9, pp. 129-163.
57. P. F. SCHOLL, D. KONGKASURIYACHAI, P. A. DEMIREV, A. B. FELDMAN, J. S. LIN, D. J. SULLIVAN and N. KUMAR, *The American Journal of Tropical Medicine and Hygiene*, 2004, 71, 546-551.
58. M. NYUNT, J. PISCIOTTA, A. B. FELDMAN, P. THUMA, P. F. SCHOLL, P. A. DEMIREV, J. S. LIN, L. SHI, N. KUMAR and D. J. SULLIVAN, *The American Journal of Tropical Medicine and Hygiene*, 2005, 73, 485-490.
59. A. Butykai, A. Orbán, V. Kocsis, D. Szaller, S. Bordács, E. Tátrai-Szekeres, L. F. Kiss, A. Bóta, B. G. Vértessy, T. Zelles and I. Kérsmárki, *Scientific Reports*, 2013, 3, 1431.
60. N. L. Garrett, R. Sekine, M. W. A. Dixon, L. Tilley, K. R. Bambery and B. R. Wood, *Physical Chemistry Chemical Physics*, 2015.
61. E. Y. Lukianova-Hleb, K. M. Campbell, P. E. Constantinou, J. Braam, J. S. Olson, R. E. Ware, D. J. Sullivan and D. O. Lapotko, *Proceedings of the National Academy of Sciences of the United States of America*, 2014, 111, 900-905.
62. E. Y. L. Hleb and D. O. Lapotko, *Theranostics*, 2014, 4, 761-769.
63. C. Romagosa, C. Menendez, M. R. Ismail, L. Quintó, B. Ferrer, P. L. Alonso and J. Ordi, *Acta Tropica*, 2004, 90, 277-284.
64. B. K. Wilson, M. R. Behrend, M. P. Horning and M. C. Hegg, *Opt. Express*, 2011, 19, 12190-12196.
65. D. M. Newman, J. Heptinstall, R. J. Matelon, L. Savage, M. L. Wears, J. Beddow, M. Cox, H. D. F. H. Schallig and P. F. Mens, *Biophysical Journal*, 2008, 95, 994-1000.

What is claimed is:

1. A diagnostic method for the detection of a biomarker in a biological sample comprising the steps of:
    performing a polymerization reaction above a lower critical solution temperature (LCST) of a polymer formed by combining a plurality of initiators, a plurality of atom transfer radically polymerizable monomers, and a biological sample containing a biomarker that serves as a catalyst for atom transfer radical polymerization reaction (ATRP), whereby the polymer formed by the monomers is precipitable at or above the lower critical solution temperature (LCST);
    determining turbidity formation; and
    determining a concentration of the biomarker in the biological sample based on the turbidity formation.

2. The method according to claim 1, wherein the biomarker is a heme-containing molecule.

3. The method according to claim 2, wherein the heme-containing molecule is one or more of hemoglobin, myoglobin, peroxidase, catalase, hemozoin, hemin, and hematin and dimers or oligomers thereof.

4. The method according to claim 3, wherein the plurality of atom transfer radically polymerizable monomers are N-isopropyl acrylamide monomers, and wherein the polymerization reaction polymerizes the N-isopropyl acrylamide monomers to form the polymer, which is poly(N-isopropyl acrylamide).

5. The method according to claim 1, wherein the step of determining the turbidity formation is performed by spectroscopy, visual observation with an eye, measurement of light scattering or optical density using a light source.

6. The method according to claim 1, wherein the step of determining the turbidity formation is performed by UV-vis spectroscopy.

7. The method according to claim 6, wherein a spectrophotometer is utilized to record extinction between 200 and 900 nm.

8. The method according to claim 1, wherein the polymerization reaction is conducted between 4° C. and 100° C.

9. The method according to claim 1, further including the step of treating the biological sample prior to combination with the plurality of initiators and plurality of monomers in order to isolate the biomarker.

10. The method according to claim 1, wherein the biological sample is one or more of blood, plasma, red blood cells, cerebrospinal fluid, feces, a biopsy sample and urine.

11. The method according to claim 1, wherein the biomarker is hemozoin.

12. The method according to claim 1, wherein the biomarker is haeme.

13. The method according to claim 1, wherein the biomarker is hemoglobin.

14. A diagnostic method for the detection of a biomarker in a biological sample comprising the steps of:
A) performing a polymerization reaction above a lower critical solution temperature (LCST) of a polymer formed by combining a plurality of initiators, a plurality of atom transfer radically polymerizable monomers, and a biological sample containing a biomarker that serves as a catalyst for an atom transfer radical polymerization reaction (ATRP), whereby the polymer formed by the monomers is precipitable at or above the lower critical solution temperature (LCST);
B) determining turbidity at i) a point in time after initiation of polymerization or ii) a time to reach a certain turbidity after the initiation, or both i) and ii), and
C) determining a concentration of the biomarker in the biological sample based on the determination made in step B.

15. The method according to claim 14, wherein the biomarker is a heme-containing molecule, wherein the heme-containing molecule is one or more of hemoglobin, myoglobin, peroxidase, catalase, hemozoin, hemin, and hematin and dimers or oligomers thereof, wherein the plurality of atom transfer radically polymerizable monomers are N-isopropyl acrylamide monomers, wherein the polymerization reaction polymerizes the N-isopropyl acrylamide monomers to form the polymer, which is poly(N-isopropyl acrylamide), wherein the step of determining the turbidity is performed by spectroscopy, visual observation with an eye, measurement of light scattering or optical density using a light source, and wherein the polymerization reaction is conducted between 4° C. and 100° C.

\* \* \* \* \*